_(12)_ United States Patent
Niitsu et al.

(10) Patent No.: US 8,003,621 B2
(45) Date of Patent: Aug. 23, 2011

(54) DRUG CARRIERS

(75) Inventors: Yoshiro Niitsu, Sapporo (JP); Lei Yu, Carlsbad, CA (US); Jian Liu, San Diego, CA (US); Gang Zhao, Vista, CA (US); Nianchun Ma, Oceanside, CA (US); Sang Van, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 12/210,098

(22) Filed: Sep. 12, 2008

(65) Prior Publication Data

US 2009/0105179 A1    Apr. 23, 2009

Related U.S. Application Data

(60) Provisional application No. 60/972,732, filed on Sep. 14, 2007, provisional application No. 61/016,431, filed on Dec. 21, 2007, provisional application No. 61/084,935, filed on Jul. 30, 2008.

(51) Int. Cl.
*A01N 61/00* (2006.01)
*A01N 43/04* (2006.01)
*A61K 9/16* (2006.01)
*G01N 33/53* (2006.01)
*C07H 21/04* (2006.01)

(52) U.S. Cl. ............. 514/44; 424/497; 424/498; 435/6; 435/7.1; 435/7.23; 435/458; 514/1; 514/2; 536/24.5

(58) Field of Classification Search ............. 435/6, 91.1, 435/458, 455, 7.1, 7.23; 514/1, 244, 2, 44; 536/23.1, 23.5, 24.5; 424/497, 498
See application file for complete search history.

(56) References Cited

U.S. PATENT DOCUMENTS

| | | | |
|---|---|---|---|
| 4,156,067 A | 5/1979 | Gould |
| 4,460,560 A | 7/1984 | Tökes et al. |
| 4,536,387 A | 8/1985 | Sakamoto et al. |
| 4,565,863 A | 1/1986 | Bollag et al. |
| 4,642,111 A | 2/1987 | Sakamoto et al. |
| 4,665,897 A | 5/1987 | Lemelson |
| 4,678,670 A | 7/1987 | Tomic |
| 4,818,542 A | 4/1989 | DeLuca et al. |
| 5,130,126 A | 7/1992 | Koyama et al. |
| 5,173,298 A | 12/1992 | Meadows |
| 5,260,066 A | 11/1993 | Wood et al. |
| 5,262,172 A | 11/1993 | Sipos |
| 5,268,180 A | 12/1993 | Morancais et al. |
| 5,288,503 A | 2/1994 | Wood et al. |
| 5,422,116 A | 6/1995 | Yen et al. |
| 5,472,954 A | 12/1995 | Loftsson |
| 5,475,006 A | 12/1995 | Burton et al. |
| 5,482,698 A | 1/1996 | Griffiths |
| 5,498,421 A | 3/1996 | Grinstaff et al. |
| 5,525,338 A | 6/1996 | Goldenberg |
| 5,534,261 A | 7/1996 | Rodgers et al. |
| 5,543,150 A | 8/1996 | Bologna et al. |
| 5,543,158 A | 8/1996 | Gref et al. |
| 5,583,020 A | 12/1996 | Sullivan |
| 5,609,629 A | 3/1997 | Fearnot et al. |
| 5,614,178 A | 3/1997 | Bloom et al. |
| 5,635,207 A | 6/1997 | Grinstaff et al. |
| 5,639,473 A | 6/1997 | Grinstaff et al. |
| 5,648,506 A | 7/1997 | Desai et al. |
| 5,651,986 A | 7/1997 | Brem et al. |
| 5,733,572 A | 3/1998 | Unger et al. |
| 5,744,155 A | 4/1998 | Friedman et al. |
| 5,744,460 A | 4/1998 | Müller et al. |
| 5,753,261 A | 5/1998 | Fernandez et al. |
| 5,770,222 A | 6/1998 | Unger et al. |
| 5,783,566 A | 7/1998 | Mislick |
| 5,785,976 A | 7/1998 | Westesen et al. |
| 5,801,191 A | 9/1998 | Bressi et al. |
| 5,811,119 A | 9/1998 | Mehta et al. |
| 5,820,879 A | 10/1998 | Fernandez et al. |
| 5,824,049 A | 10/1998 | Ragheb et al. |
| 5,827,886 A | 10/1998 | Hersh |
| 5,843,642 A | 12/1998 | Dmitrovsky et al. |
| 5,858,987 A | 1/1999 | Beer-Romero et al. |
| 5,879,713 A | 3/1999 | Roth et al. |
| 5,886,026 A | 3/1999 | Hunter et al. |
| 5,916,596 A | 6/1999 | Desai et al. |
| 5,925,379 A | 7/1999 | Mandeville, III et al. |
| 5,942,230 A | 8/1999 | Wu et al. |
| 5,977,163 A | 11/1999 | Li et al. |
| 5,994,341 A | 11/1999 | Hunter et al. |
| 5,994,495 A | 11/1999 | Gozzini et al. |
| 6,013,240 A | 1/2000 | Behr et al. |
| 6,025,337 A | 2/2000 | Truong et al. |

(Continued)

FOREIGN PATENT DOCUMENTS

EP    0 932 399    1/2006

(Continued)

OTHER PUBLICATIONS

Crooke, S., Ann. Rev. Medicine, vol. 55, pp. 61-95 (2004).*
Peracchi et al., Rev. Med. Virolo., vol. 14, pp. 47-64 (2004).*
Chirila et al., Biomaterials, vol. 23, pp. 321-342 (2002).*
Agrawal, S. et al., Molecular Med. Today, vol. 6, pp. 72-81 (2000).*
Opalinska et al., Nature Rev., vol. 1, pp. 503-514 (2002).*
Tagami et al, Intl. J. Pharmaceutics, vol. 333, pp. 62-69 (Oct. 2006).*
Andrew, E.R., et al., "Molecular motion in solid all-trans retinoic acid (vitamin A acid) by proton NMR." Solid State Nuclear Magnetic Resonance 13, pp. 39-43, 1998.
Beljaars, L., et al. "Albumin Modified With Mannosa 6-Phosphate: A Potential Carrier for Selective Delivery of Antifibrotic Drugs to Rat and Human Hepatic Stellate Cells." Hepatology vol. 29, No. 5, pp. 1486-1493, 1999.

(Continued)

*Primary Examiner* — Jane Zara
(74) *Attorney, Agent, or Firm* — Knobbe, Martens, Olson & Bear LLP

(57) ABSTRACT

Compositions that can include a cationic polymeric carrier, targeting agent, and therapeutic agent are disclosed herein. The therapeutic agent may have a therapeutic activity such as inhibiting fibrosis within a target organ or tissue or inhibiting the growth of a cancer cell.

26 Claims, 10 Drawing Sheets

U.S. PATENT DOCUMENTS

| | | | |
|---|---|---|---|
| 6,030,941 A | 2/2000 | Summerton et al. | |
| 6,037,463 A | 3/2000 | Uhlmann et al. | |
| 6,043,094 A | 3/2000 | Martin et al. | |
| 6,060,082 A | 5/2000 | Chen et al. | |
| 6,087,385 A | 7/2000 | Pershadsingh et al. | |
| 6,096,070 A | 8/2000 | Ragheb et al. | |
| 6,110,485 A | 8/2000 | Olejnik et al. | |
| 6,124,133 A | 9/2000 | Taylor et al. | |
| 6,150,461 A | 11/2000 | Takei et al. | |
| 6,159,591 A | 12/2000 | Beihoffer et al. | |
| 6,165,440 A | 12/2000 | Esenaliev | |
| 6,177,274 B1 | 1/2001 | Park et al. | |
| 6,187,315 B1 | 2/2001 | Falcon | |
| 6,200,597 B1 | 3/2001 | Mehta et al. | |
| 6,200,956 B1 | 3/2001 | Scherman et al. | |
| 6,214,345 B1 | 4/2001 | Firestone et al. | |
| 6,217,912 B1 | 4/2001 | Park et al. | |
| 6,231,960 B1 | 5/2001 | Dyer et al. | |
| 6,238,917 B1 | 5/2001 | Hendry et al. | |
| 6,248,363 B1 | 6/2001 | Patel et al. | |
| 6,248,791 B1 | 6/2001 | Ailhaud et al. | |
| 6,251,428 B1 | 6/2001 | Yoo | |
| 6,258,275 B1 | 7/2001 | Freitag et al. | |
| 6,262,107 B1 | 7/2001 | Li et al. | |
| 6,267,985 B1 | 7/2001 | Chen et al. | |
| 6,290,974 B1 | 9/2001 | Swaisgood et al. | |
| 6,294,192 B1 | 9/2001 | Patel et al. | |
| 6,309,663 B1 | 10/2001 | Patel et al. | |
| 6,312,694 B1 | 11/2001 | Thorpe et al. | |
| 6,312,727 B1 | 11/2001 | Schacht et al. | |
| 6,328,988 B1 | 12/2001 | Uhrich | |
| 6,342,219 B1 | 1/2002 | Thorpe et al. | |
| 6,344,206 B1 | 2/2002 | Nguyen et al. | |
| 6,372,245 B1 | 4/2002 | Bowman et al. | |
| 6,383,471 B1 | 5/2002 | Chen et al. | |
| 6,403,056 B1 | 6/2002 | Unger | |
| 6,407,178 B1 | 6/2002 | Kolbe et al. | |
| 6,416,758 B1 | 7/2002 | Thorpe et al. | |
| 6,441,025 B2 | 8/2002 | Li et al. | |
| 6,455,062 B1 | 9/2002 | Olejnik et al. | |
| 6,462,064 B1 | 10/2002 | Pfahl et al. | |
| 6,471,968 B1 | 10/2002 | Baker, Jr. et al. | |
| 6,472,507 B1 | 10/2002 | Fischer et al. | |
| 6,491,953 B1 | 12/2002 | Sojka et al. | |
| 6,495,532 B1 | 12/2002 | Bathurst et al. | |
| 6,495,677 B1 | 12/2002 | Ramasamy et al. | |
| 6,506,411 B2 | 1/2003 | Hunter et al. | |
| 6,509,323 B1 | 1/2003 | Davis et al. | |
| 6,515,017 B1 | 2/2003 | Li et al. | |
| 6,517,847 B2 | 2/2003 | Dow et al. | |
| 6,521,252 B1 | 2/2003 | Byk et al. | |
| 6,524,583 B1 | 2/2003 | Thorpe et al. | |
| 6,537,579 B1 | 3/2003 | Desai et al. | |
| 6,544,544 B2 | 4/2003 | Hunter et al. | |
| 6,569,463 B2 | 5/2003 | Patel et al. | |
| 6,586,524 B2 | 7/2003 | Sagara | |
| 6,592,894 B1 | 7/2003 | Zarif et al. | |
| 6,599,513 B2 | 7/2003 | Deckers | |
| 6,605,298 B1 | 8/2003 | Leigh et al. | |
| 6,605,639 B1 | 8/2003 | Tamura et al. | |
| 6,610,841 B1 | 8/2003 | Warren | |
| 6,645,528 B1 | 11/2003 | Straub et al. | |
| 6,652,886 B2 | 11/2003 | Ahn et al. | |
| 6,656,734 B1 | 12/2003 | Bischoff et al. | |
| 6,676,941 B2 | 1/2004 | Thorpe et al. | |
| 6,680,047 B2 | 1/2004 | Klaveness et al. | |
| 6,696,038 B1 | 2/2004 | Mahato et al. | |
| 6,712,617 B2 | 3/2004 | Detmar et al. | |
| 6,716,452 B1 | 4/2004 | Piccariello et al. | |
| 6,716,652 B1 | 4/2004 | Ortlieb et al. | |
| 6,730,334 B2 | 5/2004 | Zhao | |
| 6,730,699 B2 | 5/2004 | Li et al. | |
| 6,740,336 B2 | 5/2004 | Trubetskoy et al. | |
| 6,764,698 B1 | 7/2004 | Byun et al. | |
| 6,774,116 B2 | 8/2004 | Gilbert et al. | |
| 6,783,760 B1 | 8/2004 | Thorpe et al. | |
| 6,808,720 B2 | 10/2004 | Unger | |
| 6,812,218 B2 | 11/2004 | Herscovici et al. | |
| 6,833,004 B2 | 12/2004 | Ishii et al. | |
| 6,855,770 B2 | 2/2005 | Pinchuk et al. | |
| 6,869,973 B2 | 3/2005 | Garvey et al. | |
| 6,884,430 B1 | 4/2005 | Crouzet et al. | |
| 6,884,789 B2 | 4/2005 | Davis et al. | |
| 6,897,281 B2 | 5/2005 | Lubnin et al. | |
| 6,908,624 B2 | 6/2005 | Hossainy et al. | |
| 6,908,626 B2 | 6/2005 | Cooper et al. | |
| 6,923,988 B2 | 8/2005 | Patel et al. | |
| 6,927,206 B2 | 8/2005 | Patt | |
| 6,936,272 B2 | 8/2005 | Martin et al. | |
| 6,958,241 B2 | 10/2005 | Martin et al. | |
| 6,962,992 B2 | 11/2005 | Martin et al. | |
| 6,965,025 B2 | 11/2005 | Gaarde et al. | |
| 6,977,268 B2 | 12/2005 | D'Amato | |
| 6,994,862 B2 | 2/2006 | Jeong et al. | |
| 6,994,979 B2 | 2/2006 | Reed et al. | |
| 6,998,115 B2 | 2/2006 | Langer et al. | |
| 7,005,254 B2 | 2/2006 | Demo et al. | |
| 7,008,979 B2 | 3/2006 | Schottman | |
| 7,015,040 B2 | 3/2006 | Wolff et al. | |
| 7,018,655 B2 | 3/2006 | Lele et al. | |
| 7,045,356 B2 | 5/2006 | Trubetskoy et al. | |
| 7,060,498 B1 | 6/2006 | Wang | |
| 7,060,724 B2 | 6/2006 | Li et al. | |
| 7,064,127 B2 * | 6/2006 | Friedman et al. | 514/252.18 |
| 7,067,109 B1 | 6/2006 | Thorpe et al. | |
| 7,067,249 B2 | 6/2006 | Kung et al. | |
| 7,071,163 B2 | 7/2006 | Sokoloff et al. | |
| 7,074,389 B2 | 7/2006 | Frankenberger et al. | |
| 7,087,394 B2 | 8/2006 | Johnson et al. | |
| 7,091,192 B1 | 8/2006 | Davis et al. | |
| 7,094,572 B2 | 8/2006 | Ramanathan et al. | |
| 7,094,810 B2 | 8/2006 | Sant et al. | |
| 7,098,030 B2 | 8/2006 | Rozema et al. | |
| 7,101,576 B2 | 9/2006 | Hovey et al. | |
| 7,101,985 B2 | 9/2006 | Elledge et al. | |
| 7,101,995 B2 | 9/2006 | Lewis et al. | |
| 7,109,021 B2 | 9/2006 | Johnson et al. | |
| 7,122,202 B2 | 10/2006 | Allen et al. | |
| 7,129,346 B2 | 10/2006 | Gee et al. | |
| 7,132,458 B2 | 11/2006 | Burton et al. | |
| 7,138,430 B2 | 11/2006 | Garvey | |
| 7,144,880 B2 | 12/2006 | Glick | |
| 7,163,927 B2 | 1/2007 | Dobie et al. | |
| 7,176,277 B2 | 2/2007 | Reed et al. | |
| 7,196,145 B2 | 3/2007 | Ignatious | |
| 7,199,107 B2 | 4/2007 | Dobie et al. | |
| 7,223,837 B2 | 5/2007 | De Groot et al. | |
| 7,223,909 B2 | 5/2007 | Hauptmann et al. | |
| 7,253,273 B2 | 8/2007 | Collingwood | |
| 7,262,221 B2 | 8/2007 | Uhrich et al. | |
| 7,265,186 B2 | 9/2007 | Zhao | |
| 7,267,829 B2 | 9/2007 | Kirby et al. | |
| 7,270,808 B2 | 9/2007 | Cheng et al. | |
| 7,276,348 B2 | 10/2007 | Glick | |
| 7,282,576 B2 | 10/2007 | Riegel et al. | |
| 7,297,515 B1 | 11/2007 | Szankasi et al. | |
| 7,297,786 B2 | 11/2007 | McCray et al. | |
| 7,306,923 B2 | 12/2007 | Brys et al. | |
| 7,316,811 B2 | 1/2008 | Zhao et al. | |
| 7,316,816 B2 | 1/2008 | Yang et al. | |
| 7,329,431 B2 | 2/2008 | Ishii | |
| 7,329,638 B2 | 2/2008 | Yang et al. | |
| 7,332,159 B2 | 2/2008 | Labhasetwar | |
| 7,332,276 B2 | 2/2008 | Sutherland et al. | |
| 7,332,281 B2 | 2/2008 | Morris et al. | |
| 7,341,850 B2 | 3/2008 | Liu et al. | |
| 7,342,046 B2 | 3/2008 | Wang et al. | |
| 7,344,844 B2 | 3/2008 | Johnson et al. | |
| 7,344,882 B2 | 3/2008 | Lee et al. | |
| 7,345,027 B2 | 3/2008 | Tolentino et al. | |
| 7,345,178 B2 | 3/2008 | Nunes et al. | |
| 7,358,223 B2 | 4/2008 | Zhao et al. | |
| 7,361,752 B2 | 4/2008 | Heidenreich et al. | |
| 7,371,384 B2 | 5/2008 | Gerber et al. | |
| 7,371,822 B2 | 5/2008 | Ramanathan et al. | |
| 7,371,841 B2 | 5/2008 | Julius et al. | |
| 7,374,930 B2 | 5/2008 | Oh et al. | |

| | | |
|---|---|---|
| 7,375,096 B1 | 5/2008 | Davis et al. |
| 7,378,386 B2 | 5/2008 | Thorpe et al. |
| 7,381,410 B2 | 6/2008 | Krasnoperov et al. |
| 7,381,416 B2 | 6/2008 | Erdelmeir et al. |
| 7,381,535 B2 | 6/2008 | Perez et al. |
| 7,390,505 B2 | 6/2008 | Gustow et al. |
| 7,404,969 B2 | 7/2008 | Chen et al. |
| 7,405,227 B2 | 7/2008 | Kun et al. |
| 7,405,302 B2 | 7/2008 | Hutchinson et al. |
| 7,410,502 B2 | 8/2008 | Ellingsen et al. |
| 7,431,949 B2 | 10/2008 | Neis et al. |
| 7,517,913 B2 | 4/2009 | Papaioannou et al. |
| 7,557,094 B2 | 7/2009 | Wadstein |
| 2002/0012998 A1 | 1/2002 | Gonda et al. |
| 2002/0026060 A1* | 2/2002 | Belloni et al. ............ 548/452 |
| 2002/0041898 A1 | 4/2002 | Unger et al. |
| 2003/0064094 A1 | 4/2003 | Frankenberger et al. |
| 2003/0073619 A1 | 4/2003 | Mahato et al. |
| 2003/0096739 A1 | 5/2003 | Morris |
| 2003/0147958 A1 | 8/2003 | Ahn et al. |
| 2003/0161791 A1 | 8/2003 | Bentley et al. |
| 2003/0215395 A1 | 11/2003 | Yu et al. |
| 2004/0028682 A1 | 2/2004 | Border et al. |
| 2004/0048260 A1 | 3/2004 | Chang et al. |
| 2004/0071654 A1 | 4/2004 | Anderson et al. |
| 2004/0138154 A1 | 7/2004 | Yu et al. |
| 2004/0142474 A1 | 7/2004 | Mahato et al. |
| 2004/0147443 A1 | 7/2004 | Renault |
| 2004/0162235 A1 | 8/2004 | Trubetskoy et al. |
| 2005/0037200 A1 | 2/2005 | Wallach |
| 2005/0153337 A1 | 7/2005 | Manoharan |
| 2005/0165227 A1 | 7/2005 | Vlahov et al. |
| 2005/0220859 A1 | 10/2005 | Frankenberger et al. |
| 2005/0256051 A1 | 11/2005 | Morris |
| 2005/0265961 A1 | 12/2005 | Langer et al. |
| 2006/0093674 A1 | 5/2006 | Slobodkin et al. |
| 2006/0127482 A1 | 6/2006 | Fewell et al. |
| 2006/0147376 A1 | 7/2006 | Yu et al. |
| 2006/0211642 A1 | 9/2006 | McSwiggen et al. |
| 2006/0258751 A1 | 11/2006 | Zhao et al. |
| 2007/0020761 A1 | 1/2007 | Yu et al. |
| 2007/0072171 A1 | 3/2007 | Yu et al. |
| 2007/0207966 A1 | 9/2007 | Kim et al. |
| 2007/0243157 A1 | 10/2007 | Tanaka et al. |
| 2007/0269891 A9 | 11/2007 | Tanaka et al. |
| 2008/0145338 A1 | 6/2008 | Anderson et al. |
| 2008/0193512 A1 | 8/2008 | Niitsu et al. |
| 2008/0207553 A1* | 8/2008 | Zhao et al. ............ 514/44 |
| 2008/0220056 A1* | 9/2008 | Arthur et al. ............ 424/450 |
| 2008/0312174 A1 | 12/2008 | Yu et al. |
| 2009/0105179 A1 | 4/2009 | Yu et al. |
| 2010/0028416 A1 | 2/2010 | Yu et al. |
| 2010/0210715 A1 | 8/2010 | Zhao et al. |

FOREIGN PATENT DOCUMENTS

| | | |
|---|---|---|
| EP | 1279682 | 8/2008 |
| JP | 5-503076 | 5/1993 |
| JP | 2002-47211 | 2/2002 |
| JP | 2003-528131 | 9/2003 |
| JP | 2004-524371 A | 8/2004 |
| JP | 2004-382791 | 12/2004 |
| JP | 2005-531564 | 10/2005 |
| JP | 2006-522158 A | 9/2006 |
| WO | WO 96/17948 | 6/1996 |
| WO | WO 97/33618 | 9/1997 |
| WO | WO 97/45069 | 12/1997 |
| WO | WO 01/68081 | 9/2001 |
| WO | WO 02/44321 * | 6/2002 |
| WO | WO 02/083186 | 10/2002 |
| WO | WO 02/092600 | 11/2002 |
| WO | WO 03/097647 | 11/2003 |
| WO | WO 2004/065636 | 8/2004 |
| WO | WO 2004/090108 | 10/2004 |
| WO | WO 2006/041617 | 4/2006 |
| WO | WO 2006/066001 | 6/2006 |
| WO | WO 2006/068232 | 6/2006 |
| WO | WO 2006/069782 | 7/2006 |
| WO | WO 2007/051303 | 5/2007 |
| WO | WO 2007/084797 | 7/2007 |

OTHER PUBLICATIONS

Bielinska, el al., "Application of membrane-based dendrimer/DNA complexes for solid phase transfection in vitro and in vivo." Biomaterials, 21: 877·887, 2000.

Bledi, et al, "Culturing neuronal cells on surfaces coated by a novel polyethyleneimine-based polymer". Brain Res. Protocols. vol. 5, pp. 282-289, 2000.

Boussif, et al., "A versatile vector for gene and oligonucleotide transfer into cells in culture and in vivo: Polyethylenimine". Proc. Natl Acad Sci USA, vol. 92, pp. 7297-7301, 1995.

Chang, et al., "Surfection: a new platform for transfected cell arrays". Nucleic Acid Res., pp. 32:1-6, 2004.

Clark, et al. "Cationic Lipid-Mediated Gene Transfer: Current Concepts," Curr. Opin. Mol. Ther., vol. 1, No. 2, pp. 158-176, Apr. 1999 (abstract only).

De Semir, et al. "Non-viral vector-mediated uptake, distribution, and stability of chimeraplasts in human airway epithelial cells". J. Gene. Med vol. 4, pp. 308-322, 2002.

Dwyer, et al. "Attachment of PC12 cells to Adhesion Substratum Induces the Accumulation of Glucose Transporters (GLUTs) and Stimulates Glucose Metabolism". Neurochem Res, 23: 1107-1116, 1998.

Friedman, Scott L., "Targeting siRNA to Arrest Fibrosis". Nature Biotechnology, vol. 26, No. 4, April 208, pp. 399-400, 2008.

Godbey, et al., "Poly(ethylenimine)-mediated transfection: A new paradigm for gene delivery". J. Biomed. Mater. Res., 51: 321-328, 2000.

Gosselin, et al., "Efficient Gene Transfer Using Reversibly Cross-Linked Low Molecular Weight Polyethylenimine". Bioconjugate Chem., vol. 12, pp. 989-994, 2001.

International Search Report and Written Opinion dated Jun. 2, 2009 for International Application No. PCT/US2008/076287, filed Sep. 12, 2008.

Kang, J.X., et al., A Leaf. "Mannose-6-phosphateyinsulin-like growth factor-II receptor is a receptor for retinoic acid". Proc. Natl. Acad. Sci., vol. 95, pp. 13671-13676, 1998; vol. 98, pp. 15393-15394, 2001.

Kircheis, et al. "Coupling of Cell-Binding Ligands to Polyethylenimine for Targeted Gene Delivery," Gene Therapy, vol. 4, pp. 409-418, 1997.

Marschall, et al., "Transfer of YACs up to 2.3 Mb intact into human cells with polyethylenimine". Gene Therapy, 6: 1634-1637, 1999.

Petersen, et al., "Poly(ethylenimine-co-L-lactamide-co-succinamide): A Biodegradable Polyethylenimine Derivative with an Advantageous pH-Dependent Hydrolytic Degradation for Gene Delivery". Bioconjugate Chem., 13:812-821, 2002.

Pollard, et al. "Polyethylenimine but Not Cationic Lipids Promotes transgene Delivery to the Nucleus in Mammalian Cells". J. Biol. Chem., vol. 278, pp. 7507-7511, 1998.

Santel, et al., "A Novel siRNA-lipoplex technology for RNA interference in the mouse vascular endothelium". Gene Therapy, vol. 13, pp. 1222-1234, 2006.

Sato, et al., Supplementary Text and Figures from "Resolution of Liver Cirrhosis Using Vitamin A-coupled Liposomes to Deliver siRNA Against a Collagen-specific Chaperone". Nature Biotechnology, vol. 26, No. 4, pp. 431-442, 2008.

Sato, et al., "Resolution of Liver Cirrhosis Using Vitamin A-coupled Liposomes to Deliver siRNA Against a Collagen-specific Chaperone". Nature Biotechnology, vol. 26, No. 4, pp. 431-442, 2008.

Segura, et al., "Surface-Tethered DNA Complexes for Enhanced Gene Delivery". Bioconjugate Chemistry, 13: 621-629, 2002.

Singh, et al. "Liposome encapsulated vitamin A compounds exhibit greater stability and diminished toxicity." Biophysical Chemistry, vol. 73, pp. 155-162, 1998.

Vancha, et al., "Use of polyethyleneimine polymer in cell culture as attachment factor and lipofection enhancer". BMC Biotechnology, 4, 23: 1-12, 2004.

Wassall, S.R., et al. "Retinoid-Phospholipid Interactions As Studied by Magnetic Resonance" Bulletin of Magnetic Resonance, vol. 9 No. 3, pp. 85-89, 1987.

Zheng, et al., "Transfection of Cells Mediated by Biodegradable Polymer Materials with Surface-Bound Polyethyleneimine". Biotechnol Prog., 16: 254·257, 2000.

Ziauddin, et al., "Microarrays of cells expressing defined cDNAs". Nature, 411: 107-110, 2001.

International Search Report dated Mar. 28, 2006 for PCT Application No. PCT/JP2005/023619 filed Dec. 22, 2005.

International Preliminary Report on Patentability dated Mar. 26, 2007 for PCT Application No. PCT/JP2005/023619 filed Dec. 22, 2005 with Japanese-language claims and English-language translation of claims appended.

Blomhoff, Rune, et al., Hepatic Uptake of [$^3$H] Retinol Bound to the Serum Retinol Binding Protein Involves Both Parenchymal and Perisinusoidal Stellate Cells. The Journal of Biological Chemistry. vol. 260, No. 25, pp. 13571-13575, 1985.

Blomhoff, Rune, et al., Newly Administered [$^3$H] Retinol is Transferred from Hepatocytes to Stellate Cells in Liver for Storage. Experimental Cell Research, vol. 150, pp. 186-193, 1984.

Dixon et al., Nomenclature of Retinoids. Pure & Appl. Chem., vol. 55, No. 4, pp. 721-726, 1983.

Fortuna, V.A., et al., Hepatic Stellate Cells Uptake of Retinol Associated with Retinol-Binding Protein or With Bovine Serum Albumin. Journal of Cellular Biochemistry, vol. 90, No. 4, pp. 792-805, 2003.

Kamps, Jan, A.A.M., et al., Massive targeting of liposomes, surface-modified with anionized albumins, to hepatic endothelial cells. Proceedings of the National Academy of Sciences of the United States of America, vol. 94, No. 21, pp. 11681-11685, 1997.

Kikuchi, Hiroshi, Liposomes based on nanotechnology—Past, present, and future, Part II. Pharm Tech Japan, vol. 19, No. 3, pp. 419-433, 2003.

Li, D. et al., Liver fibrogenesis and the role of hepatic stellate cells: new insights and prospects for therapy. Journal of Gastroenterology and Hepatology, vol. 14, No. 7, pp. 618-633, 1999.

Sasaki, Hiroyoshi, et al., Induction of Heat Shock Protein 47 Synthesis by TGF-β and IL-1β Via Enhancement of the Heat Shock Element Binding Activity of Heat Shock Transcription Factor 1. The Journal of Immunology, vol. 168, pp. 5178-5183, 2002.

Tsuji, Hideki, et al., Targeting of liposomes surface-modified with glycyrrhizin to the liver—I. Preparation and biological disposition. Chemical & Pharmaceutical Bulletin, vol. 39, No. 4, pp. 1004-1008, 1991.

Wu, Jian, et al., Modification of liposomes for liver targeting. Journal of Hepatology, vol. 24, No. 6, pp. 757-763, 1996.

Aigner A. J., Delivery Systems for the Direct Application of siRNAs to Induce RNA Interference (RNAi) in Vivo. Biomed and Biotech, ID 71659, pp. 1-15, 2006.

Castaigne et al., All-*trans* retinoic acid as a differentiation therapy for acute promyelocytic leukemia: I. Clinical results. Blood, vol. 76, pp. 1704-1709, 1990.

Choi et al. Inhibition of tumor growth by biodegradable microspheres containing all-trans-retinoic acid in a human head-and-neck cancer xenograft. Int. J. Cancer, 107, 145-148, 2003.

Dallas et al., RNAi: A novel antisense technology and its therapeutic potential. AV. Med Sci Monit, vol. 12, pp. RA67-RA74, 2006.

Eichman et al., The use of PAMAM dendrimers in the efficient transfer of genetic material into cells. Pharm. Sci. Technol. Today, vol. 3, No. 7, pp. 232-245, 2000.

Fingl et al., The Pharmacological Basis of Therapeutics, Fifth Edition, MacMillan Publishing Co, 1975. Cover and Contents Pages Only.

Fire et al., Potent and specific genetic interference by double-stranded RNA in Caenorhabditis elegans. Nature, vol. 391, pp. 806-811, 1998.

Goodman, et al., Extraction and recombination studies of the interaction of retinol with human plasma retinol-binding protein. Journal of Lipid Research, vol. 13, pp. 338-347, 1972.

Greene et al., Protective Groups in Organic Synthesis, Third Edition, John Wiley & Sons, 1999. Cover and Contents Pages Only.

Giguere et al. Identification of a receptor for the morphogen retinoic acid. Nature, vol. 330, pp. 624-629, 1987.

Houglum et al. Two Different cis-acting Regulatory Regions Direct Cell-specific Transcription of the Collagen $\alpha_1$ (1) Gene in Hepatic Stellate Cells and in Skin and Tendon Fibroblasts. J. Clin. Invest., vol. 96, pp. 2269-2276, 1995.

Huang et al. Use of all-*trans* retinoic acid in the treatment of acute promyelocytic leukemia. Blood, vol. 72, pp. 567-572, 1988.

International Preliminary Report on Patentability and Written Opinion dated Mar. 16, 2010 for PCT Application No. PCT/US2008/076287 filed Sep. 12, 2008.

International Search Report dated May 27, 2008 for PCT Application No. PCT/JP2008/056735, filed Mar. 28, 2008, and English-language translation.

International Preliminary Report on Patentability and Written Opinion dated Oct. 6, 2009 for PCT Application No. PCT/JP2008/056735, filed Mar. 28, 2008, and English-language translation dated Oct. 13, 2009.

International Search Report dated Apr. 7, 2009 for PCT Application No. PCT/JP2009/001148, filed Mar. 16, 2009, and English-language translation.

International Preliminary Report on Patentability and Written Opinion dated Sep. 21, 2010 for PCT Application No. PCT/JP2008/056735, filed Mar. 28, 2008, and English-language translation dated Nov. 2, 2010.

Kim et al. Apoptosis induced by retinoic acid in Hep3B cells in vitro. Cancer Lett., vol. 107, pp. 149-159, 1996.

Kim, W.J., et al. Efficient siRNA delivery using water soluble lipopolymer for anti-angiogenic gene therapy. J Control Release, vol. 118, pp. 357-363, 2007.

Li et al., Delivery of RNA Interference. Cell Cycle, vol. 5, pp. 2103-2109, 2006.

Lim Y. B., et al., Cationic Hyperbranched Poly (amino ester): A Novel Class of DNA Condensing Molecule with Cationic Surface, biodegradable Three-Dimensional Structure, and Tertiary Amine Groups in the Interior. J. Am. Chem. Soc., vol. 123, No. 10, pp. 2460-2461, 2001.

Lynn, et al., Accelerated Discovery of Synthetic Transfection Vectors: Parallel Synthesis and Screening of a Degradable Polymer Library. J. Am. Chem. Soc., vol. 123, pp. 8155-8156, 2001.

March J., Advanced Organic Chemistry Third Edition, pp. 711-712, 1985.

Massaro D., et al., Noninvasive delivery of small inhibitory RNA and other reagents to pulmonary alveoli in mice. Am J Physiol Long Cell Mol Physiol, vol. 287, pp. L1066-L1070, 2004.

Moss, G.P., Biochemical Nomenclature and Related Documents, 2$^{nd}$ Ed. Portland Press, pp. 247-251, 1992.

Nastruzzi, Liposome-associated retinoic acid. Increased in vitro antiproliferative effects on neoplastic cells. FEBS Letters, vol. 259, No. 2, pp. 293-296, 1990.

Petkovich M. Regulation of gene expression by vitamin A: the role of nuclear retinoic acid receptors. Annu Rev. Nutr, vol. 12, pp. 443-471, 1990.

Wald, G. Molecular basis of visual excitation. Science, vol. 162, pp. 230-239, 1968.

Zhang S., et al. Cationic lipids and polymers mediated vectors for delivery of siRNA. J Control Release, vol. 123, pp. 1-10, 2007.

Akinc et al., A combinatorial library of lipid-like materials for delivery of RNAi therapeutics. Nature Biotechnology, pp. 1-9, 2008.

Akinc et al., Supplementary Information for a combinatorial library of lipid-like materials for delivery of RNAi therapeutics. Nature Biotechnology, pp. 1-9, 2008.

Forrest et al., A Degradable Polyethylenimine Derivative with Low Toxicity for Highly Efficient Gene Delivery. Bioconjugate Chem., vol. 14, pp. 934-940, 2003.

Leng et al., Highly branched HK peptides are effective carriers of siRNA. J Gene Med, vol. 7, pp. 977-986, 2005.

Manfredini et al., Retinoic Acid Conjugates as Potential Antitumor Agents: Synthesis and Biological Activity of Conjugates with Ara-A, Ara-C, 3(2H)-Furanone, and Aniline Mustard Moieties. J Med Chem., vol. 23, pp. 3851-3857, 1997.

Park et al., All-*trans*-retinoic acid (ATRA)-grafted polymeric gene carriers for nuclear translocation and cell growth control. Biomaterials, vol. 30, pp. 2642-2652, 2009.

Schiffelers et al., Cancer siRNA therapy by tumor selective delivery with ligand-targeted sterically stabilized nanoparticle. Nucleic Acids Research, vol. 32, No. 19, pp. 1-10, 2004.

\* cited by examiner

A

B

C

A - Retinol + Cy3-siRNA (25;1, w/w)
B - Polymer 5 + Cy3-siRNA (2.5:1, w/w)
C - Retinol + Polymer 5 + Cy3-siRNA (25:2:1, w/w)

A - siRNA alone
B - Polymer 5 + siRNA (2.5/1)
C - Polymer 5 + siRNA (5/1)
D - Retinol + Polymer 5 + siRNA (80/2.5/1 w/w ratio respective to siRNA)
E - Retinol + Polymer 5 + siRNA (120/2.5/1 w/w ratio respective to siRNA)
F - Retinol + Polymer 5 + siRNA (320/5/1 w/w ratio respective to siRNA)

A - Blank
B - siRNA
C - Polymer 5
D - Retinol + Polymer 5 + siRNA (62/2/1, 1µg siRNA)
E - Retinol + Polymer 5 + siRNA (62/2/1, 2.5µg siRNA)
F - Retinol + Polymer 5 + siRNA (62/2/1, 5µg siRNA)
G - Retinol + Polymer 5 + siRNA (62/4/1, 1µg siRNA)
H - Retinol + Polymer 5 + siRNA (62/4/1, 2.5µg siRNA)

A - Polymer 2
B - Polymer 2/siegfp(5/1)
C - Polymer 2/siHSP-47(5/1)
D - Polymer 2/siHSP-47(10/1)
E - Polymer 4/siHSP-47(5/1)
F - Polymer 4/siHSP-47(10/1)

A - Polymer 4

B - Polymer 4/siHSP47 (5/1,1mg/kg)

C - Polymer 4/siHSP47 (10/1,1mg/kg)

A - 0.2%TritonX-100

B - Polymer 2/siRNA

C - Polymer 3/siRNA

D - Polymer 4/siRNA

DRUG CARRIERS

RELATED APPLICATION INFORMATION

This application claims priority to U.S. Provisional Application Ser. Nos. 60/972,732, filed on Sep. 14, 2007; 61/016,431, filed on Dec. 21, 2007; and 61/084,935, filed on Jul. 30, 2008; all of which are incorporated herein by reference in their entireties for all purposes.

SEQUENCE LISTING

The present application is being filed along with a Sequence Listing in electronic format. The Sequence Listing is provided as a file entitled NDTCO-099A-SequenceListing.TXT, created Sep. 9, 2008, which is 1.35 Kb in size. The information in the electronic format of the Sequence Listing is incorporated herein by reference in its entirety.

BACKGROUND

1. Field

Disclosed herein are compositions and methods related to the fields of organic chemistry, pharmaceutical chemistry, biochemistry, molecular biology and medicine. In particular, embodiments disclosed herein relate to compositions and methods for delivering an active agent into a cell, and to the use of the compositions for the treatment and alleviation of diseases and disorders characterized by fibrosis.

2. Description of the Related Art

Fibrosis, or the development of excess fibrous connective tissue within the body, has been associated with a number of diseases and disorders such as hepatic fibrosis, pancreatic fibrosis, vocal cord scarring, and numerous forms of cancer.

Various approaches have been taken in an attempt to inhibit fibrosis in an organ or tissue. One approach can be to inhibit the activation of one or more stellate cells, wherein activation of such cells is characterized by an increased production of extracellular matrix (ECM). Other approaches may relate to inhibiting the production of collagen, such as by promoting collagen degradation or controlling collagen metabolism. It may be difficult, however, to target a particular organ or tissue in need thereof.

SUMMARY

Some embodiments described herein are directed to a therapeutic composition that can include a cationic polymeric carrier, a targeting agent operatively associated with the cationic polymeric carrier, wherein the targeting agent includes a retinoid, and a therapeutic agent operatively associated with the cationic polymeric carrier, wherein the therapeutic agent exhibits a therapeutic activity upon delivery to a target organ or tissue, and wherein the therapeutic activity is selected from inhibiting fibrosis within the target organ or tissue and inhibiting the growth of a cancer cell within the target organ or tissue.

Some embodiments relate to a therapeutic composition as described herein, and further including at least one selected from a pharmaceutically acceptable excipient and a diluent.

Some embodiments provide a method for treating a condition characterized at least in part by abnormal fibrosis that can include administering a therapeutically effective amount of a therapeutic composition described herein to a subject in need thereof.

Other embodiments provide the use of a therapeutic composition described herein for treating a condition characterized at least in part by abnormal fibrosis.

Still other embodiments provide a therapeutic composition described herein for treating a condition characterized at least in part by abnormal fibrosis.

These and other embodiments are described in greater detail below.

DETAILED DESCRIPTION

Figure 1:
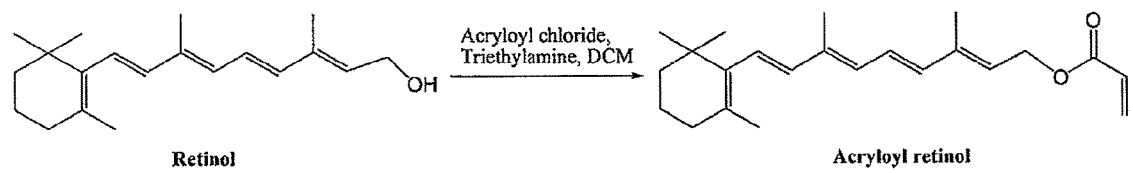
FIG. 1 illustrates a reaction scheme for the preparation of a modified retinol.

Unless defined otherwise, all technical and scientific terms used herein have the same meaning as is commonly understood by one of ordinary skill in the art. All patents, applications, published applications and other publications referenced herein are incorporated by reference in their entirety. In the event that there are a plurality of definitions for a term herein, those in this section prevail unless stated otherwise.

The term "cationic polymeric carrier" as used herein refers to a positively-charged polymer (e.g., homopolymer or copolymer) that may be operatively associated with one or more agents. A cationic polymeric carrier facilitates the transport of the one or more agents with which it is operatively associated from one part of the body to a target cell or tissue and/or into a target cell or tissue. Those skilled in the art will appreciate that, in determining the charge of the polymeric carrier, any targeting agent and/or therapeutic gent that is operatively associated with the polymeric carrier is not considered to be part of the cationic polymeric carrier. In other words, any charge carried by any targeting agent and/or therapeutic agent operatively associated with the polymeric carrier is ignored when determining that the polymeric carrier is positively-charged.

"Microparticle" refers to a particle that has a size that in the range of approximately 100 nm to approximately 1000 mm in all dimensions. A microparticle can have any shape and any morphology.

"Nanoparticle" refers to a particle that has a size that in the range of approximately 100 nm to approximately 1 nm n in all dimensions. A nanoparticle can have any shape and any morphology. Examples of nanoparticles include nanopowders, nanoclusters, nanocrystals, nanospheres, nanofibers, and nanotubes.

The term "targeting agent" refers to a compound that exhibits selectivity for a particular target organ or tissue. A targeting agent is capable of directing a composition, with which it is operatively associated, to a particular target organ or tissue. A targeting agent can be operatively associated with at least one cationic polymeric carrier and/or other agent.

A "retinoid" is a member of the class of compounds consisting of four isoprenoid units joined in a head-to-tail manner, see G. P. Moss, "Biochemical Nomenclature and Related Documents," 2nd Ed. Portland Press, pp. 247-251 (1992). "Vitamin A" is the generic descriptor for retinoids exhibiting qualitatively the biological activity of retinol. As used herein, retinoid refers to natural and synthetic retinoids including first generation, second generation, and third generation retinoids. Examples of naturally occurring retinoids include, but are not limited to, (1) 11-cis-retinal, (2) all-trans retinol, (3) retinyl palmitate, (4) all-trans retinoic acid, and (5) 13-cis-retinoic acids. Furthermore, the term "retinoid" encompasses retinols, retinals, and retinoic acids.

The term "therapeutic" refers to the alleviation, prevention, or inhibition of any undesired signs or symptoms of a disease or condition, to any extent. Such undesired signs may include those that worsen the subject's overall feeling of well-being or appearance. This term does not necessarily indicate total cure or abolition of the disease or condition. A "therapeutic agent" is a compound that, upon administration to a mammal in a therapeutically effective amount, provides a therapeutic benefit to the mammal. A therapeutic agent may be referred to herein as a drug. Those skilled in the art will appreciate that the term "therapeutic agent" is not limited to drugs that have received regulatory approval. A "therapeutic agent" can be operatively associated with at least one liposome carrier and/or other agent.

"Fibrosis" is used herein in its ordinary sense and refers to the development of fibrous scar-like connective tissue in an organ or tissue as part of a reparative or reactive process. "Abnormal fibrosis" refers to the development of fibrous scar-like connective tissue in an organ or tissue to an extent that it impairs the function of the organ or tissue.

As used herein, "linker" and "linking group" refer to one or more atoms that connect one chemical moiety to another chemical moiety. Examples of linking groups include relatively low molecular weight groups such as amide, ester, carbonate and ether, as well as higher molecular weight linking groups such as polyethylene glycol (PEG).

Where at least two molecules are "operatively associated" it means that the molecules are in electronic interaction with each other. Such interaction may take the form of a chemical bond, including, but not limited to, a covalent bond, a polar covalent bond, an ionic bond, an electrostatic association, a coordinate covalent bond, an aromatic bond, a hydrogen bond, a dipole, or a van der Waals interaction. Those of ordinary skill in the art understand that the relative strengths of such interactions may vary widely.

As used herein, "$C_m$ to $C_n$" in which "m" and "n" are integers refers to the number of carbon atoms in an alkyl, alkenyl or alkynyl group or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "m" to "n", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "m" and "n" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain fully saturated (no double or triple bonds) hydrocarbon group. The alkyl group may have 1 to 50 carbon atoms (whenever it appears herein, a numerical range such as "1 to 50" refers to each integer in the given range; e.g., "1 to 50 carbon atoms" means that the alkyl group may consist of 1 carbon atom, 2 carbon atoms, 3 carbon atoms, etc., up to and including 50 carbon atoms, although the present definition also covers the occurrence of the term "alkyl" where no numerical range is designated). The alkyl group may also be a medium size alkyl having 1 to 30 carbon atoms. The alkyl group could also be a lower alkyl having 1 to 5 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl and the like.

The alkyl group may be substituted or unsubstituted. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl (mono-, di- and tri-substituted haloalkyl), haloalkoxy (mono-, di- and tri-substituted haloalkoxy), trihalomethanesulfonyl, trihalomethanesulfonamido, and amino, including mono- and di-substituted amino groups, and the protected derivatives thereof.

As used herein, "alkenyl" refers to an alkyl group that contains in the straight or branched hydrocarbon chain one or more double bonds. An alkenyl group may be unsubstituted or substituted. When substituted, the substituent(s) may be selected from the same groups disclosed above with regard to alkyl group substitution unless otherwise indicated.

As used herein, "alkynyl" refers to an alkyl group that contains in the straight or branched hydrocarbon chain one or more triple bonds. An alkynyl group may be unsubstituted or substituted. When substituted, the substituent(s) may be selected from the same groups disclosed above with regard to alkyl group substitution unless otherwise indicated.

A "heteroalkyl" as used herein refers to an alkyl group as described herein in which one or more of the carbons atoms in the backbone of alkyl group has been replaced by a heteroatom such as nitrogen, sulfur and/or oxygen.

A "heteroalkenyl" as used herein refers to an alkenyl group as described herein in which one or more of the carbons atoms in the backbone of alkenyl group has been replaced by a heteroatom, for example, nitrogen, sulfur and/or oxygen.

A "heteroalkynyl" as used herein refers to an alkynyl group as described herein in which one or more of the carbons atoms in the backbone of alkynyl group has been replaced by a heteroatom such as nitrogen, sulfur and/or oxygen.

As used herein, "aryl" refers to a carbocyclic (all carbon) monocyclic or multicyclic aromatic ring system that has a fully delocalized pi-electron system. Examples of aryl groups include, but are not limited to, benzene, naphthalene and azulene. The ring of the aryl group may have 5 to 50 carbon atoms. The aryl group may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl (mono-, di- and tri-substituted haloalkyl), haloalkoxy (mono-, di- and tri-substituted haloalkoxy), trihalomethanesulfonyl, trihalomethanesulfonamido, and amino, including mono- and di-substituted amino groups, and the protected derivatives thereof, unless the substituent groups are otherwise indicated.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The ring of the heteroaryl group may have 5 to 50 atoms. The heteroaryl group may be substituted or unsubstituted. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl (mono-, di- and tri-substituted haloalkyl), haloalkoxy (mono-, di- and tri-substituted haloalkoxy), trihalomethanesulfonyl, trihalomethanesulfonamido, and amino, including mono- and di-substituted amino groups, and the protected derivatives thereof.

As used herein, "cycloalkyl" refers to a completely saturated (no double bonds) mono- or multi-cyclic hydrocarbon ring system. When composed of two or more rings, the rings may be joined together in a fused, bridged or spiro-connected fashion. Cycloalkyl groups may range from $C_3$ to $C_{10}$, in other embodiments it may range from $C_3$ to $C_8$. A cycloalkyl group may be unsubstituted or substituted. Typical cycloalkyl groups include, but are in no way limited to, cyclopropyl, cyclobutyl, cyclopentyl, cyclohexyl, and the like. If substituted, the substituent(s) may be an alkyl or selected from those substituents indicated above with respect to substitution of an alkyl group unless otherwise indicated.

As used herein, "cycloalkenyl" refers to a cycloalkyl group that contains one or more double bonds in the ring although, if there is more than one, the double bonds cannot form a fully delocalized pi-electron system in the ring (otherwise the group would be "aryl," as defined herein). When composed of two or more rings, the rings may be connected together in a fused, bridged or spiro-connected fashion. A cycloalkenyl group may be unsubstituted or substituted. When substituted, the substituent(s) may be an alkyl or selected from the substituents disclosed above with respect to alkyl group substitution unless otherwise indicated.

As used herein, "cycloalkynyl" refers to a cycloalkyl group that contains one or more triple bonds in the ring. When composed of two or more rings, the rings may be joined together in a fused, bridged or spiro-connected fashion. A cycloalkynyl group may be unsubstituted or substituted. When substituted, the substituent(s) may be an alkyl or selected from the substituents disclosed above with respect to alkyl group substitution unless otherwise indicated.

As used herein, "heterocyclyl" and "heteroalicyclyl" refer to a stable 3- to 18 membered ring which consists of carbon atoms and from one to five heteroatoms selected from the group consisting of nitrogen, oxygen and sulfur. The "heterocyclyl" or "heteroalicyclyl" may be monocyclic, bicyclic, tricyclic, or tetracyclic ring system, which may be joined together in a fused, bridged or spiro-connected fashion; and the nitrogen, carbon and sulfur atoms in the "heterocyclyl" or "heteroalicyclyl" may be optionally oxidized; the nitrogen may be optionally quaternized; and the rings may also contain one or more double bonds provided that they do not form a fully delocalized pi-electron system throughout all the rings. Heterocyclyl and heteroalicyclyl groups may be unsubstituted or substituted. When substituted, the substituent(s) may be one or more groups independently selected from the group consisting of alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, haloalkyl (mono-, di- and tri-substituted haloalkyl), haloalkoxy (mono-, di- and tri-substituted haloalkoxy), trihalomethanesulfonyl, trihalomethanesulfonamido, and amino, including mono- and di-substituted amino groups, and the protected derivatives thereof. Examples of such "heteroalicyclic" or "heteroalicyclyl" include but are not limited to, azepinyl, acridinyl, carbazolyl, cinnolinyl, 1,3-dioxin, 1,3-dioxane, 1,4-dioxane, 1,2-dioxolanyl, 1,3-dioxolanyl, 1,4-dioxolanyl, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazolinyl, imidazolidine, isoxazoline, isoxazolidine, oxazoline, oxazolidine, oxazolidinone, thiazoline, thiazolidine, morpholinyl, oxiranyl, piperidinyl N-Oxide, piperidinyl, piperazinyl, pyrrolidinyl, pyrrolidone, pyrrolidione, 4-piperidonyl, pyrazoline, pyrazolidinyl, 2-oxopyrrolidinyl, tetrahydropyran, 4H-pyran, tetrahydrothiopyran, thiamorpholinyl, thiamorpholinyl sulfoxide, thiamorpholinyl sulfone, and their benzo-fused analogs (e.g., benzimidazolidinone, tetrahydroquinoline, 3,4-methylenedioxyphenyl).

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents.

Unless otherwise indicated, when a substituent is deemed to be "optionally substituted," or "substituted" it is meant that the substitutent is a group that may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl (mono-, di- and tri-substituted haloalkyl), haloalkoxy (mono-, di- and tri-substituted haloalkoxy), trihalomethanesulfonyl, trihalomethanesulfonamido, and amino, including mono- and di-substituted amino groups, and the protected derivatives thereof. The protecting groups that may form the protective derivatives of the above substituents are known to those of skill in the art and may be found in references such as Greene and Wuts, Protective Groups in Organic Synthesis, 3$^{rd}$ Ed., John Wiley & Sons, New York, N.Y., 1999, which is hereby incorporated by reference in its entirety.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound having one or more double bond(s) generating geometrical isomers that can be defined as E or Z each double bond may independently be E or Z or a mixture thereof. Likewise, all tautomeric forms are also intended to be included.

As used herein, the abbreviations for any protective groups, amino acids and other compounds are, unless indicated otherwise, in accord with their common usage, recognized abbreviations, or the IUPAC-IUP Commission on Biochemical Nomenclature (See, Biochem. 11:942-944 (1972)).

Embodiments disclosed herein are directed to a therapeutic composition that can include a cationic polymeric carrier, a targeting agent operatively associated with the carrier, and a therapeutic agent operatively associated with the carrier.

Various cationic polymeric carriers can be used in the compositions disclosed herein. Suitable cationic polymers are known to those skilled in the art. In some embodiments, the cationic polymeric carrier can include a homopolymer, such as a linear or branched homopolymer. In an embodiment, the cationic polymeric carrier may include poly-L-lysine. In other embodiments, the cationic polymeric carrier may include branched or linear polyethyleneimine (PEI). In still other embodiments, the cationic polymeric carrier may include a mixture of at least two polymers. In yet still other embodiments, the cationic polymeric carrier may include a copolymer, such as a linear or branched copolymer.

The cationic polymeric carrier may include a variety of recurring units. In an embodiment, the cationic polymeric carrier can include a recurring unit of the Formula (I):

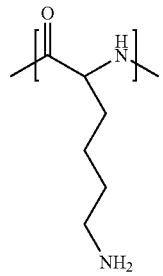

(I)

When the cationic polymeric carrier includes a recurring unit of Formula (I), the carrier may be poly-L-lysine (PLL).

In other embodiments, the cationic polymeric carrier may include one or more recurring units selected from Formulae (II), (III), (IV), (V) and (VI):

(II)

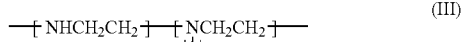

(III)

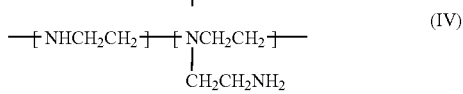

(IV)

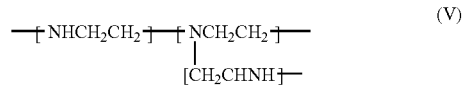

(V)

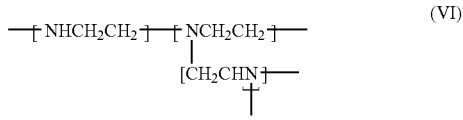

(VI)

When the cationic polymeric carrier includes a recurring unit of Formulae (II), (III), (IV), (V) and/or (VI), the carrier may be polyethyleneimine (PEI). The PEI can be linear or branched.

Various molecular weights of PEI can be used. In some embodiments, the molecular weight of the recurring cationic PEI unit can be in the range of about 200 to about 25,000 Daltons. In an embodiment, the recurring cationic PEI unit can have a molecular weight in the range of about 400 to about 5,000 Daltons. In another embodiment, the recurring cationic PEI unit can have a molecular weight in the range of about 600 to about 2,000 Daltons. In an embodiment, the recurring cationic PEI unit can have a molecular weight in the range of about 400 to about 1,200 Daltons. In some embodiments, the PEI can be branched and have a molecular weight greater equal to or greater than 600 Daltons. In other embodiments, the PEI can be linear and have a molecular weight less than 600 Daltons.

Other recurring units that may be included in the cationic polymeric carrier are disclosed in "CATIONIC POLYMER FORMULATIONS," U.S. Provisional Patent App. No. 60/972,732, filed Sep. 14, 2007, and which is incorporated herein by reference, and particularly for the purpose of describing such recurring units and cationic polymeric carriers. Suitable recurring units that can be incorporated into the cationic polymer include pentaethylenehexamine, N,N'-bis (2-aminopropyl)-ethylenediamine, spermine, N-(2-aminoethyl)-1,3-propanediamine, N-(3-aminopropyl)-1,3-propanediamine, N,N'-bis(2-aminoethyl)-1,3-propanediamine, poly(amidoamine) dendrimer (PAMAM), poly(propyleneimine) dendrimer (DAB-Am-16), spermidine, 1,4-bis(3-aminopropyl)piperazine, 1-(2-aminoethyl)piperazine, and tri(2-aminoethyl)amine. In some embodiments, the cationic polymeric carrier can be degradable, for example, biodegradable. In other embodiments, the cationic polymeric carrier can be non-degradable. In an embodiment, the degradable cationic polymeric carrier may include a degradable crosslinked cationic polymer. In some embodiments, the cationic polymeric carrier can be water soluble. In other embodiments, the cationic polymeric carrier can be water insoluble. In an embodiment, the degradable crosslinked cationic polymer can be a water soluble degradable crosslinked cationic polymer.

In an embodiment, the water soluble degradable crosslinked cationic polymer can include (a) a recurring polyethylene glycol (PEG) unit, (b) a recurring cationic polyethyleneimine (PEI) unit, and (c) a recurring degradable unit that comprises a side chain lipid group.

In some embodiments, the recurring polyethylene glycol unit in the water soluble degradable crosslinked cationic polymer can have a molecular weight in the range of about 50 Daltons to about 5,000 Daltons. In an embodiment, the recurring polyethylene glycol unit in the water soluble degradable crosslinked cationic polymer can have a molecular weight in the range of about 400 Daltons to about 600 Daltons.

In some embodiments, the recurring cationic PEI unit in the water soluble degradable crosslinked cationic polymer can have a molecular weight in the range of about 200 Daltons to about 25,000 Daltons. In an embodiment, the recurring cationic PEI unit in the water soluble degradable crosslinked cationic polymer can have a molecular weight in the range of about 600 Daltons to about 2,000 Daltons. In an embodiment, the recurring degradable unit can be a recurring unit of formula (VII):

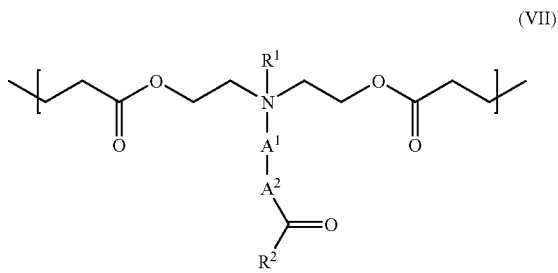

(VII)

In formula (VII), $A^1$ can be absent or an optionally substituted substituent selected from: alkyl, alkenyl, alkynyl, heteroalkyl, heteroalkenyl, heteroalkynyl and —$(CH_2)_{n1}$-D-$(CH_2)_{n2}$—; wherein n1 and n2 can be each independently 0 or an integer in the range of 1 to 10; D can be an optionally substituted substituent selected from: cycloalkyl, cycloalkenyl, cycloalkynyl, aryl, heteroaryl and heterocyclyl; $A^2$ can be absent, an oxygen atom or —$N(R^N)$, wherein $R^N$ is H or $C_{1-6}$ alkyl; $R^1$ can be an electron pair, hydrogen, or an optionally substituted substituent selected from: alkyl, alkenyl, alkynyl, heteroalkyl, heteroalkenyl, heteroalkynyl, aryl, heteroaryl, and heterocyclyl, wherein if $R^1$ is hydrogen, or an optionally substituted substituent selected from: alkyl, alkenyl, alkynyl, heteroalkyl, heteroalkenyl, heteroalkynyl, aryl, heteroaryl, and heterocyclyl, then the nitrogen atom to which $R^1$ is attached has an associated positive charge; $R^2$ can be selected from: $C_2$-$C_{50}$ alkyl, $C_2$-$C_{50}$ heteroalkyl, $C_2$-$C_{50}$ alkenyl, $C_2$-$C_{50}$ heteroalkenyl, $C_2$-$C_{50}$ alkynyl, $C_2$-$C_{50}$ heteroalkynyl, $C_5$-$C_{50}$ aryl, $C_5$-$C_{50}$ heteroaryl, $(CH_2)_{p1}$-E-$(CH_2)_{p2}$—, and sterol; wherein p1 and p2 can be each independently 0 or an integer in the range of 1 to 40; and E can be an optionally substituted substituent selected from: cycloalkyl, cycloalkenyl, cycloalkynyl, aryl, heteroaryl and heterocyclyl. In an embodiment, $R^2$ can be $C_4$-$C_{30}$ alkyl, $C_4$-$C_{30}$ alkenyl, $C_4$-$C_{30}$ alkynyl or a sterol. In another embodiment, $R^2$ can be $C_8$-$C_{24}$ alkyl, $C_4$-$C_{24}$ alkenyl, $C_4$-$C_{24}$ alkynyl or a sterol. While not wanting to be bound by theory, it is believed that the ester groups in the Formula (VII) impart improved biodegradability to the water soluble degradable crosslinked cationic polymeric carrier.

In some embodiments, $R^2$ can be a lipid group. In some embodiments, $R^2$ can be selected from oleyl, lauryl, myristyl, palmityl, margaryl, stearyl, arachidyl, behenyl and lignoceryl. In an embodiment, $R^2$ can be oleyl. In some embodiments, $R^2$ can be a sterol. In an embodiment, the sterol can be a cholesteryl moiety.

The nitrogen atom to which $R^1$ is attached in Formula (VII) can have an electron pair, a hydrogen, or an optionally substituted substituent selected from the group consisting of alkyl, alkenyl, alkynyl, heteroalkyl, heteroalkenyl, heteroalkynyl, aryl, heteroaryl, and heterocyclyl bonded to it. Those skilled in the art understand that when the nitrogen atom has an electron pair, the recurring unit of Formula (VII) above is cationic at low pH, and when $R^1$ is hydrogen, or an optionally substituted substituent selected from the group consisting of alkyl, alkenyl, alkynyl, heteroalkyl, heteroalkenyl, heteroalkynyl, aryl, heteroaryl, and heterocyclyl, the nitrogen atom has an associated positive charge.

In an embodiment, the recurring degradable unit can have the following structure:

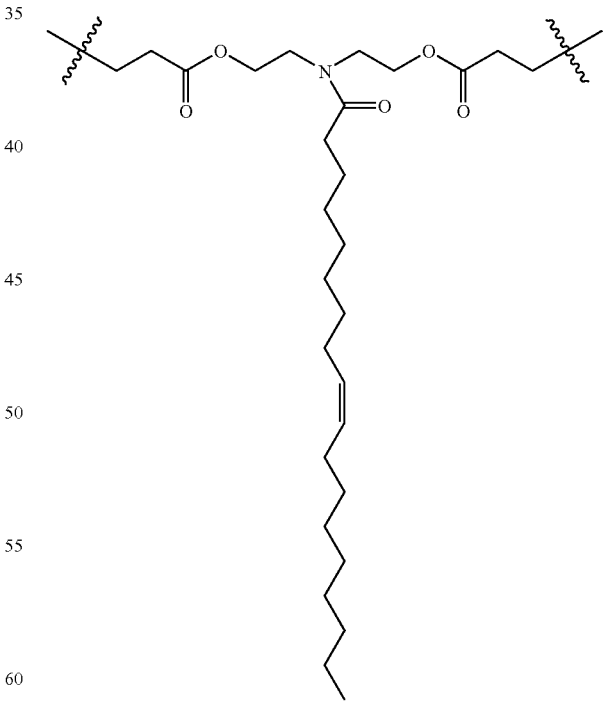

In some embodiments, the water soluble degradable crosslinked cationic polymeric carrier can include about 1 mole % to about 95 mole % of the recurring degradable unit based on the total moles of recurring units in the water soluble degradable crosslinked cationic polymeric carrier. In an embodiment, the water soluble degradable crosslinked cationic polymeric carrier can include about 30 mole % to about 90 mole % of the recurring degradable unit based on the total moles of recurring units in the water soluble degradable crosslinked cationic polymeric carrier. In some embodiments, the water soluble degradable crosslinked cationic polymeric carrier can include about 50 mole % to about 86 mole % of the recurring degradable unit based on the total moles of recurring units in the water soluble degradable crosslinked cationic polymeric carrier.

crosslinked cationic polymeric carrier can include about 5 mole % to about 30 mole % of the recurring polyethylene glycol unit based on the total moles of recurring units in the water soluble degradable crosslinked cationic polymeric carrier. In some embodiments, the water degradable crosslinked cationic polymeric carrier can include about 8 mole % to about 30 mole % of the recurring polyethylene glycol unit based on the total moles of recurring units in the water soluble degradable crosslinked cationic polymeric carrier.

An exemplary portion of a water soluble degradable crosslinked cationic polymeric carrier is shown below:

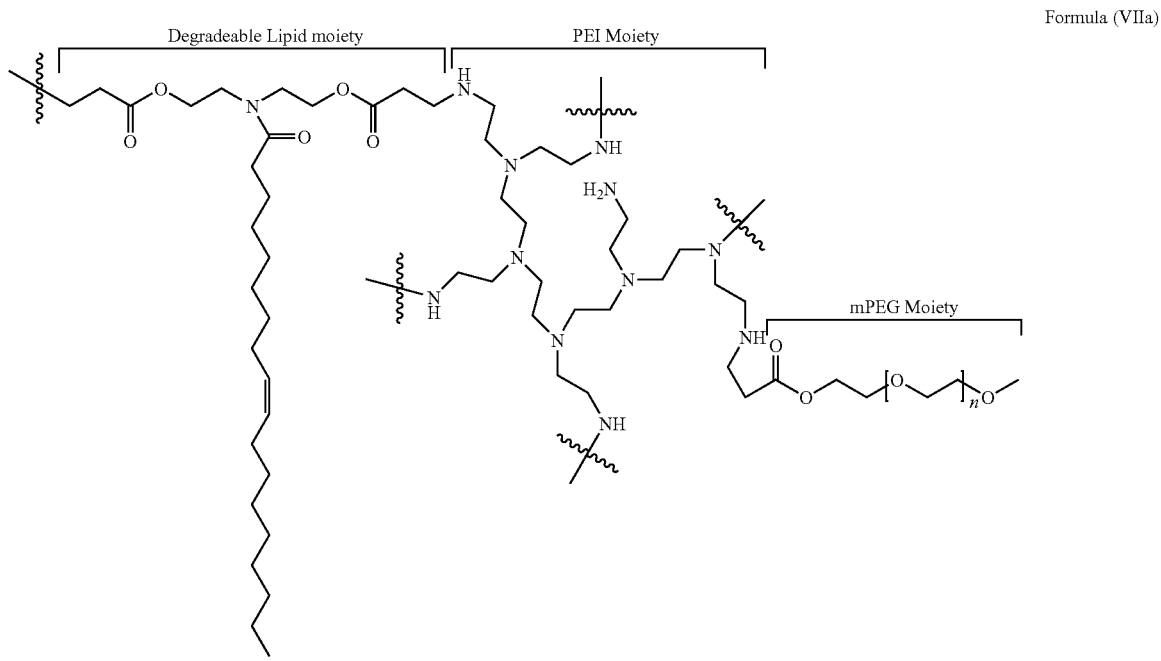

Formula (VIIa)

In an embodiment, the water soluble degradable crosslinked cationic polymeric carrier can include about 1 mole % to about 35 mole % of the recurring cationic polyethyleneimine unit based on the total moles of recurring units in the water soluble degradable crosslinked cationic polymeric carrier. In some embodiments, the water soluble degradable crosslinked cationic polymeric carrier can include about 1 mole % to about 20 mole % of the recurring cationic polyethyleneimine unit based on the total moles of recurring units in the water soluble degradable crosslinked cationic polymeric carrier. In an embodiment, the water soluble degradable crosslinked cationic polymeric carrier can include about 5 mole % to about 15 mole % of the recurring cationic polyethyleneimine unit based on the total moles of recurring units in the water soluble degradable crosslinked cationic polymeric carrier.

In an embodiment, the water soluble degradable crosslinked cationic polymeric carrier can include about 1 mole % to about 80 mole % of the recurring polyethylene glycol unit based on the total moles of recurring units in the water soluble degradable crosslinked cationic polymeric carrier. In some embodiments, the water soluble degradable crosslinked cationic polymeric carrier can include about 1 mole % to about 50 mole % of the recurring polyethylene glycol unit based on the total moles of recurring units in the water soluble degradable crosslinked cationic polymeric carrier. In an embodiment, the water soluble degradable In an embodiment, a water soluble degradable crosslinked cationic polymeric carrier can include one or more branched PEI cationic recurring units in the polymer having a molecular weight of about 1200 Daltons; one or more degradable recurring units of Formula (VII) in the polymer; and one or more polyethylene glycol recurring units in the polymer having a molecular weight of about 454 Daltons.

In an embodiment, the cationic polymeric carrier may include one or more recurring units of Formula (VIII):

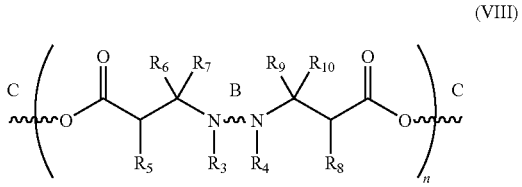

(VIII)

The linkers B and C in Formula (VIII) are each a group of atoms covalently linking the amino groups and ester groups, respectively. Each linker may contain carbon atoms and/or heteroatoms (e.g., nitrogen, oxygen, sulfur, etc.). In some embodiments, one or more of these linkers can comprise or consist of approximately 1 to 30 atoms. In an exemplary embodiment, one or more of these linkers comprises or consists of approximately 1 to 15 atoms. The linkers may be independently optionally substituted with various substituents including, but not limited to, hydrogen atoms, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. As would be appreciated by one of skill in this art, each of these groups may in turn be substituted. The groups $R_3$, $R_4$, $R_5$, $R_6$, $R_7$, $R_8$, $R_9$, and $R_{10}$ may independently be any chemical group including, but not limited to, a hydrogen atom, an alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, alkylthioether, thiol, and ureido group. In some embodiments, n is an integer in the range of from approximately 5 to about 10,000. In an exemplary embodiment, n is an integer in the range of from approximately 10 to about 500.

In an embodiment, the cationic polymeric carrier may include one or more recurring units of Formula (IX):

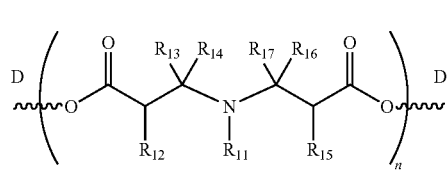

(IX)

The linker D in Formula (IX) can be a group of atoms covalently linking the ester groups. The linker may contain carbon atoms and/or heteroatoms (e.g., nitrogen, oxygen, sulfur, etc.). In some embodiments, the linker can comprise or consist of 1 to about 30 atoms. In an exemplary embodiment, the linker can be comprise or consist of 1 to about 15 long. The linker may be independently optionally substituted with various substituents including, but not limited to, hydrogen atoms, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. As would be appreciated by one of skill in this art, each of these groups may in turn be substituted. Each of $R_{11}$, $R_{12}$, $R_{13}$, $R_{14}$, $R_{15}$, $R_{16}$, and $R_{17}$ may independently be any chemical group including, but not limited to, a hydrogen atom, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, alkylthioether, thiol, and ureido group. In some embodiments, n can be an integer in the range of from approximately 5 to about 10,000. In an exemplary embodiment, n can be an integer in the range of from approximately 10 to about 500. Additional examples of recurring units of Formulae (VIII) and (IX), that can be included in the cationic polymeric carriers include, but are not limited to:

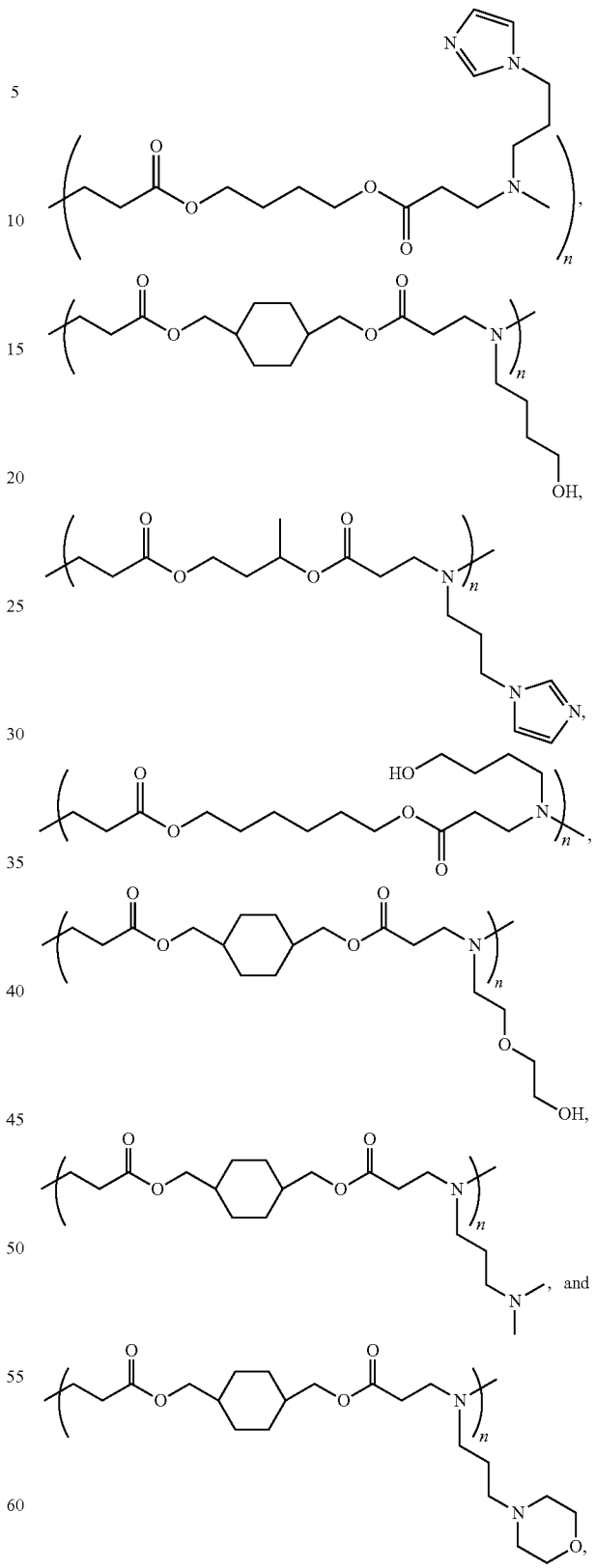

wherein n can be an integer in the range of between about 3 and about 10,000. The recurring units of Formulae (VIII) and (IX) can be substituted and include the salts thereof.

In an embodiment, the cationic polymeric carrier may include one or more recurring units of Formula (X):

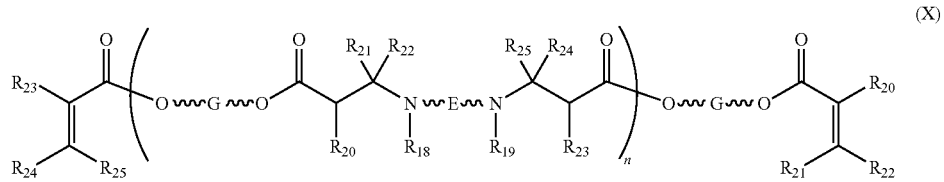

(X)

The linkers E and G in Formula (X) can be each a group of atoms covalently linking the amino groups and ester groups, respectively. Each linker may contain carbon atoms and/or heteroatoms (e.g., nitrogen, oxygen, sulfur, etc.). In some embodiments, one or more of these linkers comprise or consist of 1 to about 30 atoms long. In an exemplary embodiment, one or more linker comprise or consist of 1 to about 15 atoms. The linker may include cyclic structures including aryl and heteroaryl groups. The linkers may be substituted with various substituents including, but not limited to, hydrogen atoms, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. As would be appreciated by one of skill in this art, each of these groups may in turn be substituted. The groups $R_{18}$, $R_{19}$, $R_{20}$, $R_{21}$, $R_{22}$, $R_{23}$, $R_{24}$ and $R_{25}$ may be any chemical groups including, but not limited to, hydrogen atoms, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, alkylthioether, thiol, and ureido groups. In certain embodiments, $R_{18}$ and $R_{19}$ are the same. In other embodiments, $R_{20}$ and $R_{23}$ are the same; $R_{22}$ and $R_{24}$ are the same; and $R_{21}$ and $R_{24}$ are the same. In some embodiments, n is an integer in the range of from approximately 5 to about 10,000. In an exemplary embodiment, n is an integer in the range of from approximately 10 to about 500.

In an embodiment, the cationic polymeric carrier may include one or more recurring units of Formula (XI):

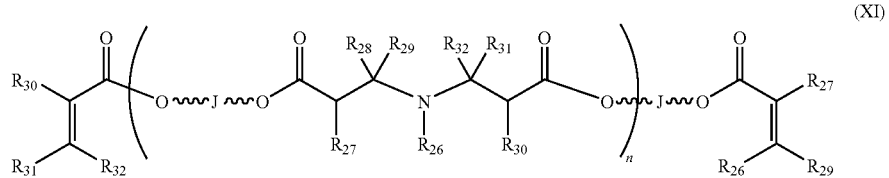

(XI)

The linker J in Formula (XI) can be a group of atoms covalently linking the acrylate moieties. The linker may contain carbon atoms or heteroatoms (e.g., nitrogen, oxygen, sulfur, etc.). In some embodiments, the linker can comprise or consist of 1 to about 30 atoms. In an exemplary embodiment, the linker can comprise or consist of 1 to about 15 atoms. In another embodiment, the linker can be approximately 2-10 atoms long. In some embodiments, the linker J is a substituted or unsubstituted, linear or branched alkyl chain. In an embodiment, the linker J may contain approximately 3-10 carbon atoms. In another embodiment, the linker J may contain approximately 3, 4, 5, 6, or 7 carbon atoms. In other embodiments, the linker J is a substituted or unsubstituted, linear or branched heteroaliphatic chain. In an embodiment, the linker J may contain approximately 3-10 atoms. In another embodiment, the linker J may contain approximately 3, 4, 5, 6, or 7 atoms. In some embodiments, the linker J includes repeating units containing oxygen and carbon atoms. The linker may be optionally substituted with various substituents including, but not limited to, hydrogen atoms, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, acyl, acetyl, and ureido groups. As would be appreciated by one of skill in this art, each of these groups may in turn be substituted. Each of $R_{26}$, $R_{27}$, $R_{28}$, $R_{29}$, $R_{30}$, $R_{31}$, and $R_{32}$ may independently be any chemical group including, but not limited to, a hydrogen atom, an alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, alkylthioether, thiol, acyl, acetyl, and ureido group. In some embodiments, $R_{26}$ can include a hydroxyl group. In other embodiments, $R_{26}$ can include an amino, alkylamino, and/or dialkylamino group. In some embodiments, n is an integer in the range from approximately 3 to about 10,000. In an exemplary embodiment, n is an integer in the range from approximately 10 to about 500.

In another embodiment, the cationic polymer can be poly{(ethylene imine)-co-[N-2-aminoethyl)ethylene imine]-co-[N—(N-cholesteryloxycabonyl-(2-aminoethyl))ethylene imine]}. Additional examples of suitable cationic polymers are disclosed in U.S. Pat. No. 6,696,038, issued Feb. 24, 2004; U.S. Patent Publication No. 2003/0073619, filed Feb. 25, 2002; U.S. Patent Publication No. 2004/0142474, filed Nov. 19, 2003; and Lynn, et al. *J. Am. Chem. Soc.* (2001), 123, 8155-8156, all of which are each hereby incorporated by reference, and in particular, for the purpose of describing suitable cationic polymers and methods for making the cationic polymers.

The cationic polymeric carrier can contain one or more chiral carbon atoms. The chiral carbon (which may be indicated by an asterisk *) can have the rectus (right handed) or the sinister (left handed) configuration, and thus the recurring unit may be racemic, enantiomeric or enantiomerically enriched.

As with the cationic polymeric carrier, various targeting agents may be used in the composition. One suitable targeting agent can include a retinoid, such as those described herein. Suitable retinoids include retinol, retinal, retinoic acid, rexinoid, or derivatives or analogs thereof. Exemplary retinoids include vitamin A, all-trans retinol, retinyl palmitate, and retinyl acetate. One example of a retinal is 11-cis-retinal. Rexinoids are retinoid compounds which are selective for retinoid X receptors (RXR). An exemplary rexinoid is retinoid bexarotene. Other retinoid derivatives and analogs include etretinate, acitretin, tazarotene, bexarotene, adapalene, and fenretinide. In some embodiments, the retinoid can be selected from retinol, retinal, retinoic acid, all-trans retinol, all-trans retinoic acid, retinyl palmitate, 11-cis-retinal and 13-cis-retinoic acid. In an embodiment, the retinoid may include vitamin A.

As mentioned previously, the targeting agent may increase the delivery selectivity of the therapeutic composition to a particular target organ or tissue. Target organs may include, for example, the liver, pancreas, kidney, lung, esophagus, larynx, bone marrow, and brain. In some embodiments, the increase in delivery selectivity may be at least about two-fold as compared to that of an otherwise comparable therapeutic composition lacking the targeting agent. In an embodiment, the increase in delivery selectivity may be at least three-fold. In some embodiments, the therapeutic compositions described herein can increase the delivery of the therapeutic agent to the target organ by at least 10% more as compared to that of an otherwise comparable therapeutic composition lacking the target agent. In other embodiments, the therapeutic compositions described herein can increase the delivery of the therapeutic agent to the target organ by at least 25% more as compared to that of an otherwise comparable therapeutic composition lacking the target agent. In yet other embodiments, the therapeutic compositions described herein can increase the delivery of the therapeutic agent to the target organ by at least 50% more as compared to that of an otherwise comparable therapeutic composition lacking the target agent. In yet still other embodiments, the therapeutic compositions described herein can increase the delivery of the therapeutic agent to the target organ by at least 75% more as compared to that of an otherwise comparable therapeutic composition lacking the target agent.

The amount of targeting agent present in the therapeutic composition can vary over a wide range. In some embodiments, the targeting agent can be about 1% to about 50% (weight/weight) of the total mass of the therapeutic composition (wherein the mass of the targeting agent is included in the total mass of the therapeutic composition). In other embodiments, the targeting agent may be about 10% to about 30% w/w of the total mass of the therapeutic composition (same basis). In still other embodiments, the targeting agent may be about 20% to about 40% w/w of the total mass of the therapeutic composition (same basis).

A variety of therapeutic agents may be included in the compositions described herein. In some embodiments, the therapeutic activity of the therapeutic agent may be inhibiting the growth of a cancer cell. The therapeutic agent may directly and/or indirectly inhibit the growth of a cancer cell. For example, the therapeutic agent may induce apoptosis by directly acting on the cancer cell. The therapeutic agent may also indirectly inhibit the growth of a cancer cell by targeting one or more fibroblast cells that supports the cancer cell. In an embodiment, the therapeutic agent may be cytotoxic.

In some embodiments, the therapeutic activity of the therapeutic agent may include inhibiting fibrosis within a target organ or tissue, such as those described previously. For example, the therapeutic agent may inhibit the activation of a stellate cell upon delivery of the therapeutic agent to a target organ or tissue. "Activation," as the term is used herein, describes an abnormal state of a stellate cell characterized by increased proliferation, decreased vitamin A concentration, and/or increased collagen production.

In some embodiments, the therapeutic agent may be an anti-cancer agent. An exemplary anti-cancer agent is paclitaxel. In some embodiments, the therapeutic agent may be a small molecule agent. In these embodiments, the therapeutic agent may be selected from a transforming growth factor beta (TGFβ) inhibitor, a matrix metalloproteinase (MMP) promoter, a hepatocyte growth factor (HGF) promoter, a tissue inhibitor of metalloproteinase (TIMP) production inhibitor, a gamma-type peroxisome proliferator-activated receptor (PPARγ) ligand, an angiotensin activity inhibitor, a platelet derived growth factor (PDGF) inhibitor, a sodium channel inhibitor, and an apoptosis inducer.

In other embodiments, the therapeutic agent may include an amino acid. In these embodiments, the therapeutic agent may be selected from siRNA, DNA, RNA, and an antisense nucleic acid. In an embodiment, the therapeutic agent can be siRNA. In some embodiments, siRNA includes RNA having 5 to 50 base pairs, preferably 10 to 35 base pairs and more preferably 19 to 27 base pairs. The siRNA may also include mixed RNA/DNA molecules or mixed protein/RNA molecules. In an embodiment, the therapeutic agent may inhibit the secretion of collagen. The therapeutic agent may, upon delivery to a target organ, substantially inhibit the activity of a tissue inhibitor of metalloproteinases (TIMP) or a molecular chaperone. In some embodiments, the molecular chaperone that is inhibited by delivery of the therapeutic agent to a target organ may collagen-specific, such as heat shock protein 47 (HSP47).

The amount of therapeutic agent present in the therapeutic composition can vary over a wide range. The therapeutic agent can be about 25% to about 75% (weight/weight) of the total mass of the therapeutic composition (wherein the mass of the therapeutic agent is included in the total mass of the therapeutic composition). In other embodiments, the therapeutic agent can be about 30% to about 60% w/w of the total mass of the therapeutic composition (same basis). In still other embodiments, the therapeutic agent can be about 40% to about 70% w/w of the total mass of the therapeutic composition (same basis).

In some embodiments, the cationic polymeric carrier may be in the form of a microparticle. In other embodiments, the cationic polymeric carrier may be in the form of a nanoparticle.

The therapeutic compositions disclosed herein may be prepared in various ways. As disclosed herein, one or more of the agents can be operatively associated with the cationic polymeric carrier through an electrostatic association. In an embodiment, the targeting agent may be operatively associated with the cationic polymeric carrier through an electrostatic association. Likewise, the therapeutic agent may be operatively associated with the cationic polymeric carrier through an electrostatic association.

Alternatively, in some embodiments, one or more of the agents may be operatively associated with the cationic polymeric carrier through a covalent bond. In some embodiments, the targeting agent and cationic polymeric carrier may be operatively associated through a covalent bond. When operatively associated through a covalent bond, the targeting agent and cationic polymeric carrier may be directly bonded to each other. In an embodiment, a retinol may be directly bonded to the cationic polymeric carrier. A variety of mechanisms known to those skilled in the art can be used to form the covalent bond between the targeting agent and cationic polymeric carrier. As an example, retinol and a cationic polymeric carrier may become directly bonded to one another through a condensation reaction. Additional methods for directly bonding a retinol to a cationic polymeric carrier are known to those skilled in the art, and may be identified by routine experimentation informed by the guidance provided herein.

In other embodiments, one or more of the agents may be operatively associated with the cationic polymeric carrier through a linking group. Examples of linking groups include relatively low molecular weight groups such as amide, ester, carbonate and ether, as well as higher molecular weight linking groups such as poly(ethylene) glycol (PEG). The linking group(s) can be introduced by modifying one or more of the targeting agent, therapeutic agent, and cationic polymeric carrier to include a moiety that forms the linking group when the targeting agent, therapeutic agent and/or cationic polymeric carrier are reacted with one another. An exemplary moiety is a double bond. The modified targeting agent, therapeutic agent, and/or carrier can then be reacted with one another using methods known to those skilled in the art, for example, via a Michael reaction (see J. March, Advanced Organic Chemistry 3rd Ed., pp. 711-712 (1985)). For example, a modified targeting agent such as a retinoid can be reacted with the poly-L-lysine and/or PEI such that the targeting agent is operatively associated with the cationic polymeric carrier through a linking group. Alternative methods for attaching a targeting agent to a cationic polymeric carrier through a linking group are known to those skilled in the art and may be identified by routine experimentation informed by the guidance provided herein.

In some embodiments, the therapeutic agent and targeting agent separately or in combination may be combined with the cationic polymeric carrier to form a mixture. The mixture can be treated (e.g., incubated) under suitable conditions to allow the targeting agent and/or therapeutic agent to become operatively associated with the cationic polymeric carrier. If desirable, one of the agents and cationic polymeric carrier can be allowed to react before the addition of the other agent. In some embodiments, the targeting agent can be combined with the cationic polymeric carrier before the addition of the therapeutic agent. In other embodiments, the therapeutic agent can be combined with the cationic polymeric carrier before the addition of the targeting agent. In still other embodiments, the targeting agent and therapeutic agent can be combined at approximately the same time with the cationic polymeric carrier.

Alternatively, the targeting agent and/or therapeutic agent can be attached to a monomer that will be used to form part of the cationic polymeric carrier. The monomer can then be polymerized using methods known to those skilled in the art to form the cationic polymeric carrier. For example, a targeting agent and/or therapeutic agent can be attached to the L-lysine monomer prior to polymerization. The resulting monomer with the attached targeting agent and/or therapeutic agent can then be polymerized using methods known to those skilled in the art to form the cationic polymeric carrier.

Various targeting agents may be operatively associated with the cationic polymeric carrier. A suitable targeting agent may be a retinoid, as disclosed above. Suitable retinoids include, but are not limited to, retinol, retinal, retinoic acid, rexinoid, and derivatives and analogs thereof, as disclosed above. In some embodiments, the targeting agent may be operatively associated with the cationic polymeric carrier through an electrostatic association. In other embodiments, the targeting agent may be operatively associated with the cationic polymeric carrier through a covalent bond. When operatively associated through a covalent bond, the targeting agent and cationic polymeric carrier may be directly bonded to each other. For example, acryloyl retinol may be directly bonded to one or more of the recurring units (e.g., a recurring unit of formulae (I), (II), (III), (IV), (V), (VI), (VII) (VIII), (IX) and/or (X)) described herein through a modified Michael addition. In other embodiments, the targeting agent and cationic polymeric carrier may be bonded to each other through a linking group, as described above.

Various therapeutic agents may be operatively associated with the cationic polymeric carrier, including those described above. In some embodiments, the therapeutic activity of the therapeutic agent may include inhibiting fibrosis within a target organ or tissue. In some embodiments, the therapeutic agent may be an anti-cancer agent. An exemplary anti-cancer agent is paclitaxel. In some embodiments, the therapeutic agent may be a small molecule agent. In these embodiments, the therapeutic agent may be selected from a transforming growth factor beta (TGFβ) inhibitor, a matrix metalloproteinase (MMP) promoter, a hepatocyte growth factor (HGF) promoter, a tissue inhibitor of metalloproteinase (TIMP) production inhibitor, a gamma-type peroxisome proliferator-activated receptor (PPARγ) ligand, an angiotensin activity inhibitor, a platelet derived growth factor (PDGF) inhibitor, a sodium channel inhibitor, and an apoptosis inducer.

In other embodiments, the therapeutic agent may include an amino acid. In these embodiments, the therapeutic agent may be selected from siRNA, DNA, RNA, and an antisense nucleic acid. In an embodiment, the therapeutic agent can be siRNA. In some embodiments, siRNA includes RNA having 5 to 50 base pairs, preferably 10 to 35 base pairs and more preferably 19 to 27 base pairs. The siRNA may also include mixed RNA/DNA molecules or mixed protein/RNA molecules. In an embodiment, the therapeutic agent may inhibit the secretion of collagen. The therapeutic agent may, upon delivery to a target organ, substantially inhibit the activity of a tissue inhibitor of metalloproteinases (TIMP) or a molecular chaperone. In some embodiments, the molecular chaperone that is inhibited by delivery of the therapeutic agent to a target organ may collagen-specific, such as heat shock protein 47 (HSP47).

In other embodiments, the therapeutic agent may be operatively associated with the cationic polymeric carrier through a covalent bond. When operatively associated through a covalent bond, the therapeutic agent and the cationic polymeric carrier may be directly bonded to each other. For example, an anti-cancer agent may be directly bonded to the cationic polymeric carrier. In an embodiment, paclitaxel can be operatively associated with the cationic polymeric carrier at the oxygen atom attached to the C2'-carbon. In another embodiment, paclitaxel can be operatively associated with the cationic polymeric carrier at the oxygen atom attached to the C7-carbon. In some embodiments, the cationic polymeric carrier can have paclitaxel attached at the oxygen atom attached to the C2'-carbon and/or the oxygen atom attached to the C7-carbon. In other embodiments, the therapeutic agent and the cationic polymeric carrier may be bonded to each other through a linking group, as described above.

The operative association of the therapeutic agent and cationic polymeric carrier, as disclosed herein, may be carried out in a number of different ways known to those skilled in the art. One method for operatively associating the therapeutic agent and the cationic polymeric carrier is by using heat (e.g., heat using a microwave method). In an embodiment, the reaction can be heated up to a temperature in the range of about 100° to about 150° C. In another embodiment, the time the materials are heated ranges from about 5 to about 40 minutes. If desired, the reaction mixture can be cooled to room temperature. These steps may be carried out manually, by automated systems, or by a combination of both.

The aforementioned reactions can take place at any suitable temperature, such as room temperature. Appropriate solvents, coupling agents, catalysts, and/or buffers as generally known to those skilled in the art and/or as described herein may be used to operatively associate the therapeutic agent, the targeting agent, and the cationic polymeric carrier.

In addition, suitable methods known to those skilled in the art can be used to isolate and/or purify the therapeutic composition. For instance, a reaction mixture can be filtered into an acidic water solution. Any precipitate that forms can then be filtered and washed with water. Optionally, the precipitate can be purified by any suitable method known to those skilled in the art. For example, the precipitate can be transferred into acetone and dissolved, and the resulting solution can be filtered again into a sodium bicarbonate solution. If desired, the resulting reaction solution can be dialyzed in water using a cellulose membrane and the polymer can be lyophilized and isolated. After formation of the therapeutic composition, any free amount of targeting agent or therapeutic agent that is not operatively associated with the carrier may also be measured. For example, thin layer chromatography (TLC) may be used to confirm the substantial absence of a free therapeutic agent remaining in the therapeutic composition.

The targeting agent and the therapeutic agent may be operatively associated with the cationic polymeric carrier at various positions relative to the cationic polymeric carrier. Such positions may be fixed (e.g., at the middle, ends or side chains of the cationic polymeric carrier) or relative, e.g., the cationic polymeric carrier may exhibit a configuration in a particular medium (such as an aqueous medium) such that it has interior and exterior portions. In an embodiment, one or more of the targeting agent and the therapeutic agent may be operatively associated with a side chain moiety of the cationic polymeric carrier. In other embodiments, one or more of the targeting agent and the therapeutic agent may be operatively associated with an end or terminal recurring unit of the cationic polymeric carrier. In yet other embodiments, one or more of the targeting agent and the therapeutic agent may be operatively associated with the middle of the cationic polymeric carrier. In still yet other embodiments, one or more of the targeting agent and the therapeutic agent may be operatively associated with the backbone of the cationic polymeric carrier. In an embodiment, one or more of the targeting agent and the therapeutic agent may be operatively associated with an exterior moiety or surface of the cationic polymeric carrier. In some embodiments, one or more of the targeting agent and the therapeutic agent may be operatively associated with an interior moiety or surface of the cationic polymeric carrier. In an embodiment, one or more of the targeting agent and the therapeutic agent can be at least partially contained within the cationic polymeric carrier. In another embodiment, one or more of the targeting agent and the therapeutic agent may be substantially completely contained within the cationic polymeric carrier.

In some embodiments, one type of agent (e.g., the therapeutic agent or the targeting agent) may be operatively associated with the cationic polymeric carrier at one part, while another type of agent (e.g., the therapeutic agent or the targeting agent) may be operatively associated with the cationic polymeric carrier at another part. As an example, the targeting agent may be operatively associated with an exterior moiety or surface of the cationic polymeric carrier and the therapeutic agent may be operatively associated with an interior moiety or surface of the cationic polymeric carrier. In the alternative, the therapeutic agent can be operatively associated with an exterior surface of the cationic polymeric carrier and the targeting agent may be operatively associated with an interior surface or the core of the cationic polymeric carrier. In other embodiments, one type of agent (e.g., the therapeutic agent or the targeting agent) may be operatively associated with the cationic polymeric carrier at approximately the same part. As an example, both agents may be associated with an interior moiety or surface of the cationic polymeric carrier. In the alternative, both agents may be associated with exterior moiety or surface of the cationic polymeric carrier. When one or more of the agents are associated with an interior moiety or surface, each agent may be partially or completely encapsulated within the cationic polymeric carrier. Those of ordinary skill in the art will recognize that the location and orientation of association may vary depending on the properties of the specific targeting agent, therapeutic agent, and cationic polymeric carrier.

In some embodiments, one or more of the targeting agent and the therapeutic agent may be operatively associated with an amino acid before the cationic polymeric carrier is formed, wherein the amino acid forms a part of the cationic polymeric carrier. In other embodiments, one or more of the targeting agent and the therapeutic agent may be operatively associated with the cationic polymeric carrier after it is formed. In some embodiments the cationic polymeric carrier may be operatively associated with the targeting agent before it is operatively associated with the therapeutic agent. In other embodiments the cationic polymeric carrier may be operatively associated with the targeting agent after it has been operatively associated with the therapeutic agent. In some embodiments, the targeting agent and therapeutic agent can both be electrostatically associated with the cationic polymeric carrier. In other embodiments, the targeting agent and therapeutic agent can both be covalently bonded to the cationic polymeric carrier. In still other embodiments, one type of agent (e.g., the targeting agent or therapeutic agent) may be electrostatically associated with the cationic polymeric carrier and another type of agent (e.g., the therapeutic agent or targeting agent) may be covalently bonded to the cationic polymeric carrier.

The therapeutic compositions disclosed herein may be prepared in various ways known to those skilled in the art. The cationic polymeric carriers disclosed herein may be prepared according to a variety of methods. Many of the cationic polymeric carriers disclosed herein, such as poly-L-lysine and polyethyleneimine (PEI), may be commercially available or prepared using methods known to those of ordinary skill in the art.

In some embodiments, a water soluble degradable crosslinked cationic polymeric carrier such as those disclosed herein may be prepared according to method disclosed in Lynn, et al. *J. Am. Chem. Soc.* 2001, 123, 8155-8156 using diacrylates as linker molecules between cationic compounds. In some embodiments, a water soluble degradable crosslinked cationic polymer that can include (a) a recurring polyethylene glycol (PEG) unit, (b) a recurring cationic polyethyleneimine (PEI) unit, and (c) a recurring degradable unit that comprises a side chain lipid group can be synthesized by dissolving a first reactant comprising recurring ethyleneimine units in an organic solvent to form a dissolved or partially dissolved polymeric reactant; reacting the dissolved or partially dissolved polymeric reactant with a degradable monomeric reactant to form a degradable crosslinked polymer, wherein the degradable monomeric reactant comprises a lipid group; and reacting the degradable crosslinked polymer with a third reactant, wherein the third reactant comprises recurring polyethylene glycol units. For example, a water soluble degradable crosslinked cationic polymer that includes the recurring backbone degradable unit of Formula (VII) can be synthesized by one method shown below. As shown in Scheme A, the compound of Formula (VIIb) may be reacted PEI with to form a degradable crosslinked cationic polymer that includes one or moieties of Formula (VIIc).

Scheme A

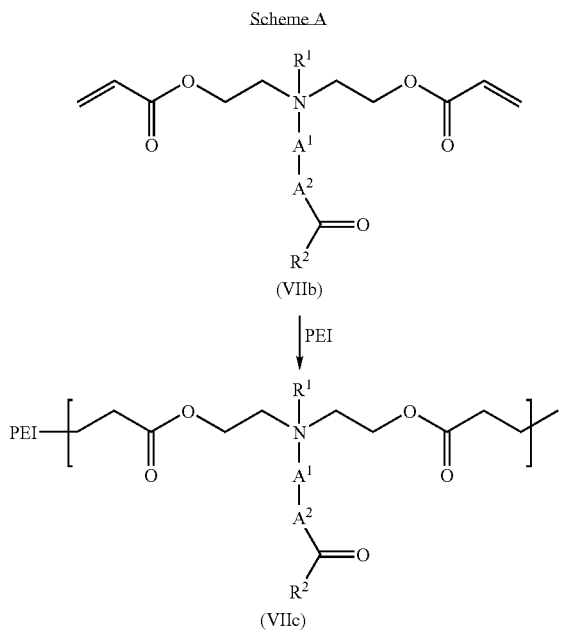

(VIIb)

↓ PEI (VIIc)

In Scheme $A^1$, $A^2$, $R^1$ and $R^2$ have the same meanings as described herein with respect to Formula (VII).

The reaction illustrated in Scheme A may be carried out by intermixing the PEI and the compound of Formula (VIIb) in a mutual solvent such as ethanol, methanol or dichloromethane with stirring; preferably at room temperature for several hours. The resulting polymer can be recovered using techniques known to those skilled in the art. For example, the solvent can be evaporated to recover the resulting polymer. This invention is not bound by theory of operation, but it is believed that the reaction between the PEI and compound of Formula (VIIb) involves a Michael reaction between one or more amines of the PEI with double bond(s) of the compound of Formula (VIIb) (see J. March, Advanced Organic Chemistry $3^{rd}$ Ed., pp. 711-712 (1985)). The compound of Formula (VIIb) shown in Scheme A may be prepared in the manner as described in U.S. Publication No. 2006/0258751, which is incorporated herein by reference, including all drawings.

The recurring units of Formulae (VIII), (IX), (X) and (XI) can be synthesized using methods known to those skilled in the art. For example, the recurring units of Formulae (VIII) and (IX) can be prepared via the conjugate addition of bis (secondary amine) or primary amine to bis(acrylate ester). The general reaction schemes are shown below in Schemes B and C.

Scheme B

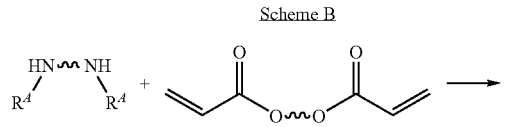

-continued

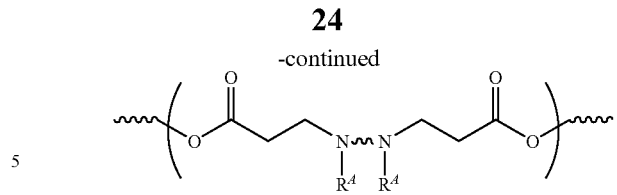

Scheme C

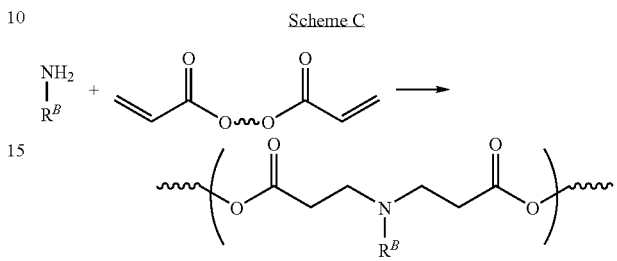

In Schemes B and C, the groups $R^A$ and $R^B$ may independently be any chemical group including, but not limited to, a hydrogen atom, an alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, alkylthioether, thiol, and ureido group. Additional examples of recurring units of Formulae (VIII), (IX), (X) and (XI) and methods of making the same are disclosed in U.S. Pat. No. 6,998,115, issued Feb. 14, 2006, entitled "BIODEGRADABLE POLY(β-AMINO ESTERS) AND USES THEREOF;" and U.S. Patent Publication No. 2008/0145338, filed Jun. 5, 2007, entitled "CROSSLINKED, DEGRADABLE POLYMERS AND USES THEREOF," which are hereby incorporated by reference for the specific purpose of describing suitable cationic polymeric carriers and methods of making the same. Additional details regarding the synthesis of cationic polymeric carriers that include a recurring unit of Formula (VIII), (IX), (X) and/or (XI) are described in "BIODEGRADABLE POLY (β-AMINO ESTERS) AND USES THEREOF," U.S. Pat. No. 6,998,115, filed Oct. 2, 2001 and/or "CROSSLINKED, DEGRADABLE POLYMERS AND USES THEREOF," U.S. Patent Publication No. 2008/0145338, filed Jun. 5, 2007.

The targeting agents disclosed herein may be commercially available or may be made according to methods known to those of skill in the art. In addition, the therapeutic agents disclosed herein may be prepared according to a variety of methods as known to those of ordinary skill in the art. Certain therapeutic agents, such as paclitaxel, may be commercially available. In some embodiments, the therapeutic agent may include a nucleic acid, such as siRNA, DNA, RNA or an antisense nucleic acid. In some embodiments, a nucleic acid may be specifically adapted to promote degradation of a particular molecule. Such a molecule may be, for example, a tissue inhibitor of metalloproteinases (TIMP) or a molecular chaperone. The molecular chaperone that is inhibited by delivery of a therapeutic agent to a target organ or tissue may be collagen-specific, such as heat shock protein 47 (HSP47). In some embodiments, siRNA may be designed with a particular sequence to recognize HSP47. Those having ordinary skill in the art will recognize that various techniques of designing nucleic acids in this manner are available and that chemically synthesized nucleic acids may be commercially available.

Another embodiment provides a pharmaceutical composition that can include one or more therapeutic compositions described herein, and further including at least one selected from a pharmaceutically acceptable excipient, a second carrier (in addition to the cationic polymeric carrier described herein), and a diluent. In some embodiments, prodrugs, metabolites, stereoisomers, hydrates, solvates, polymorphs, and pharmaceutically acceptable salts of the compounds disclosed herein (e.g., the therapeutic composition that can include a targeting agent and a therapeutic agent) are provided.

If the manufacture of pharmaceutical formulations involves intimate mixing of the pharmaceutical excipients and the active ingredient in its salt form, then it may be desirable to use pharmaceutical excipients which are non-basic, that is, either acidic or neutral excipients.

In various embodiments, the compositions disclosed herein (e.g., the therapeutic composition that can include a targeting agent and a therapeutic agent) can be used alone, in combination with other compounds disclosed herein, or in combination with one or more other agents active in the therapeutic areas described herein.

In another aspect, the present disclosure relates to a pharmaceutical composition comprising one or more physiologically acceptable surface active agents, additional carriers, diluents, excipients, smoothing agents, suspension agents, film forming substances, and coating assistants, or a combination thereof; and a composition (e.g., the therapeutic composition that can include a targeting agent and a therapeutic agent) disclosed herein. Acceptable additional carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a composition disclosed herein (e.g., the therapeutic composition that can include a targeting agent and a therapeutic agent) with other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" refers to a second chemical compound, different from and in addition to the cationic polymeric carrier, that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" refers to chemical compounds diluted in water that will dissolve the composition of interest (e.g., the therapeutic composition that can include a targeting agent and a therapeutic agent) as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. As used herein, an "excipient" refers to an inert substance that is added to a composition to provide, without limitation, bulk, consistency, stability, binding ability, lubrication, disintegrating ability, etc., to the composition. A "diluent" is a type of excipient.

The term "physiologically acceptable" refers to a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds (e.g., the therapeutic composition that can include a targeting agent and a therapeutic agent) can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions may be formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the composition can be formulated readily by combining the compositions of interest (e.g., the therapeutic composition that can include a targeting agent and a therapeutic agent) with pharmaceutically acceptable carriers well known in the art. Such carriers, which may be used in addition to the cationic polymeric carrier, enable the compositions of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the composition can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compositions may also be formulated in rectal compositions such as suppositories or retention enemas, e.g., containing conventional suppository bases such as cocoa butter or other glycerides.

In addition to the formulations described previously, the compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Disclosed herein are methods for treating a condition characterized by abnormal fibrosis, which may include administering a therapeutically effective amount of therapeutic compositions as described herein. Conditions characterized by abnormal fibrosis may include cancer and/or a fibrotic disease. Types of cancer that may be treated or ameliorated by a therapeutic composition described herein include, but are not limited to, lung cancer, pancreatic cancer, breast cancer, liver cancer, stomach cancer, and colon cancer. In an embodiment, the cancer that may be treated or ameliorated is pancreatic cancer. In another embodiment, the cancer that may be treated or ameliorated is lung cancer. Types of fibrotic disease that may be treated or ameliorated by a therapeutic composition described herein include, but are not limited to, hepatic fibrosis, hepatic cirrhosis, pancreatitis, pancreatic fibrosis, cystic fibrosis, vocal cord scarring, vocal cord mucosal fibrosis, laryngeal fibrosis, pulmonary fibrosis, idiopathic pulmonary fibrosis, cystic fibrosis, myelofibrosis, retroperitoneal fibrosis, and nephrogenic systemic fibrosis. In an embodiment, the condition that may be treated or ameliorated is hepatic fibrosis.

The compositions or pharmaceutical compositions described herein may be administered to the subject by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the active compound into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to about 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are about 0.1% to about 500%, more preferably about 25% to about 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of each active ingredient, preferably about 1 mg to about 500 mg, e.g. 5 to 200 mg. In other embodiments, an intravenous, subcutaneous, or intramuscular dose of each active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to about 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

Compositions disclosed herein (e.g., the therapeutic composition that can include a targeting agent and a therapeutic agent) can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

EXAMPLES

The following examples are provided for the purposes of further describing the embodiments described herein. Chemicals such as methanol, dichloromethane (DCM), polyethylene glycol methyl ether acrylate (PEG), Retinol and other reagents were purchased from Sigma-Aldrich chemical company. Polyethyleneimine was purchased from PolyScience, Inc. The degradable monomer of Formula (VII) was synthesized according to the general procedure reported in patent application U.S. Patent Publication No. 2006/0258751, and described herein. Water soluble degradable crosslinked cationic polymers were synthesized according to the general procedures reported in U.S. patent application Ser. No. 12/126,721, filed May 23, 2008, which is incorporated herein by reference in its entireties including any drawings.

The siRNA sequence targeting HSP-47 was purchased from Ambion, Inc.

Sense:       GCAACUAAAGACCUGGAUGtt    (SEQ ID NO: 1)

Anti-sense: ctCGUUGAUUUCUGGACCUAC    (SEQ ID NO: 2)

HeLa human cervix adenocarcinoma and B16F0 mouse skin melanoma cells were purchased from ATCC and cultured in DMEM medium with 10% FBS. GFP-expression stable cell lines were generated by transfecting GFP expression vectors into the cells and selected by hygromycin B (for HeLa-GFP) or neomycin (for B16F0-GFP).

Example 1

Acryloyl retinol was prepared according to the general scheme illustrated in FIG. 1 as follows: Retinol (302 mg, 1 mmol) was dissolved in anhydrous dichloromethane ($CH_2Cl_2$, 5 mL). Triethylamine ($Et_3N$, 0.25 mL, 1.8 mmol) and 4-di(methylamino)pyridine (DMAP, 12 mg, 0.1 mmol) were added into the retinol solution. Acryloyl chloride (0.12 mL, 96%, 1.4 mmol) was added dropwise at 0° C. into the resulting solution while stirring. After the addition, stirring was continued at 0° C. for 30 minutes. Then the solution was diluted with $CH_2Cl_2$ (15 mL) and water was added (10 mL). The organic phase was extracted and was washed with water, brine, dried with anhydrous sodium sulfate, respectively, and concentrated for chromatography purification (hexane/ethylacetate (EtOAc), 40:1) to yield acryloyl retinol (160 mg, 47%). After the chromatography, before concentration, 0.8 mg (0.5% w/w) of 4-ethoxyphenol was added to the solution of acryloyl retinol in hexane/EtOAc, to prevent polymerization from occurring. The resulting solution was kept in refrigerator (−20° C.) from light. Identity of the product was confirmed by NMR spectroscopy.

Example 2

Figure 2:
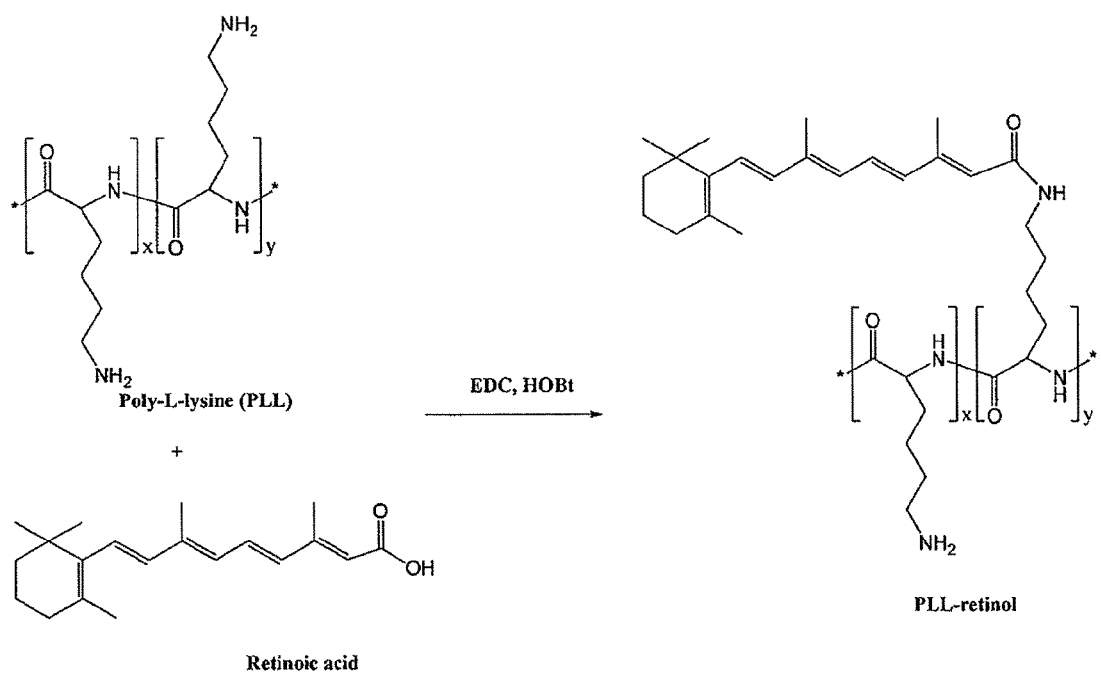
FIG. 2 illustrates a reaction scheme for the preparation of a cationic polymeric carrier that includes poly-L-lysine and a retinoic acid.

A poly-L-lysine (PLL)-retinol composition was prepared according to the general scheme illustrated in FIG. 2 as follows: Poly-L-lysine (PLL, 100 mg) was dissolved in DMF (10 mL). Retinoic acid (5 mg), EDC (30 mg) and HOBt (5 mg) were added into the solution. The resulting solution was placed under a microwave condition for 5 minutes. The reaction mixture was poured into 0.2N HCl solution. White precipitate was isolated by centrifugation. The precipitate was re-dissolved in 0.5 M sodium bicarbonate solution. The solution was placed under dialysis against water. The product PLL-retinol was lyophilized. Identity of the product was confirmed by $^1$H-NMR.

Example 3

Figure 3:
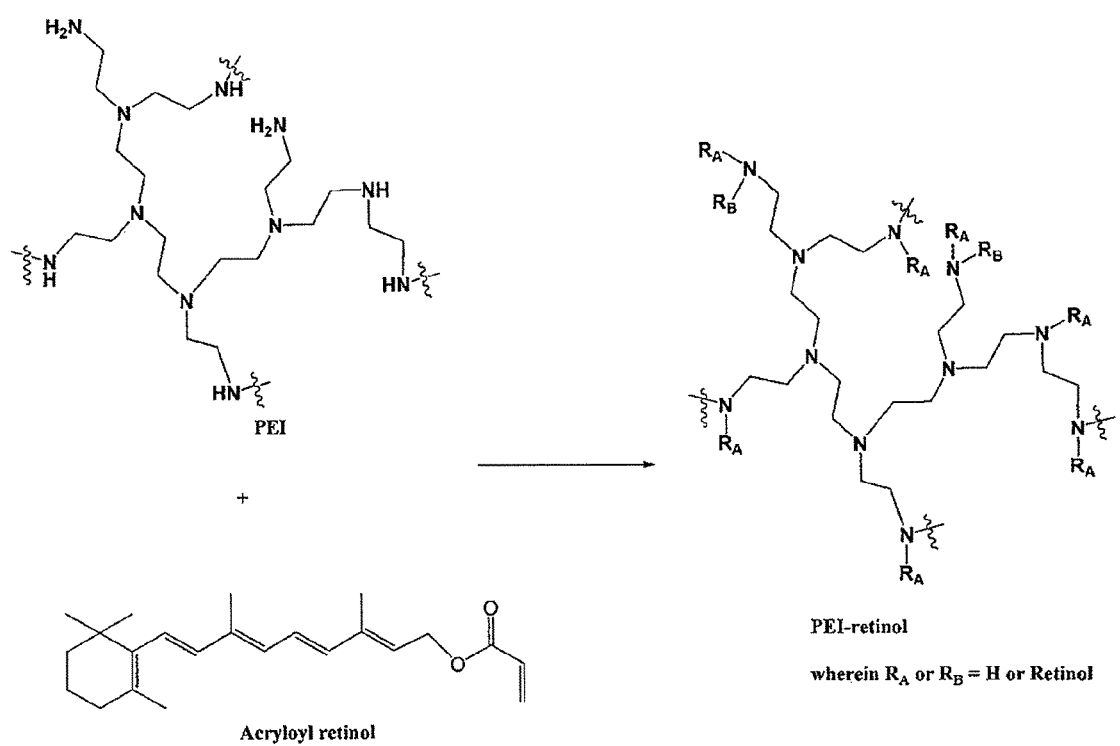
FIG. 3 illustrates a reaction scheme for the preparation of a cationic polymeric carrier that includes branched polyethylenimine and a modified retinol compound.

A poly(ethylene imine) (PEI)-retinol composition was prepared according to the general scheme illustrated in FIG. 3 as follows: PEI600 (50 mg) was dissolved in ethanol (4 mL). A solution of acryloyl retinol (5 mg) in ethanol (1 mL) was dropwise added into the solution. Ethanol (1 mL) was added as a rinse into the resulting solution, which was then stirred for 4 hours. The resulting mixture was placed under vacuum to remove ethanol to yield PEI600-retinol. Identity of the product was confirmed by $^1$H-NMR. The same product, PEI600-retinol, was also obtained and confirmed by $^1$H-NMR using various amounts of starting material(s). For example, PEI600 (50 mg) and acryloyl retinol (10 mg) or PEI600 (1200 mg) and acryloyl retinol (10 mg).

Example 4

A PEI-retinol composition was prepared according to the general scheme illustrated in FIG. 3 as follows: PEI1200 (50 mg) was dissolved in ethanol (4 mL). A solution of acryloyl retinol (5 mg) in ethanol (1 mL) was dropwise added into the solution. Ethanol (1 mL) was added as a rinse into the resulting solution, which was then stirred for 4 hours. The resulting mixture was placed under vacuum to remove ethanol to yield PEI200-retinol. Identity of the product was confirmed by $^1$H-NMR.

Example 5

A PEI-retinol composition was prepared according to the general scheme illustrated in FIG. 3 as follows: PEI2000 (50 mg) was dissolved in ethanol (4 mL). A solution of acryloyl retinol (5 mg) in ethanol (1 mL) was dropwise added into the solution. Ethanol (1 mL) was added as a rinse into the resulting solution, which was then stirred for 4 hours. The resulting mixture was placed under vacuum to remove ethanol to yield PEI2000-retinol. Identity of the product was confirmed by $^1$H-NMR. The same product, PEI2000-retinol, was also obtained and confirmed by $^1$H-NMR starting with 1200 mg of PEI2000.

Example 6

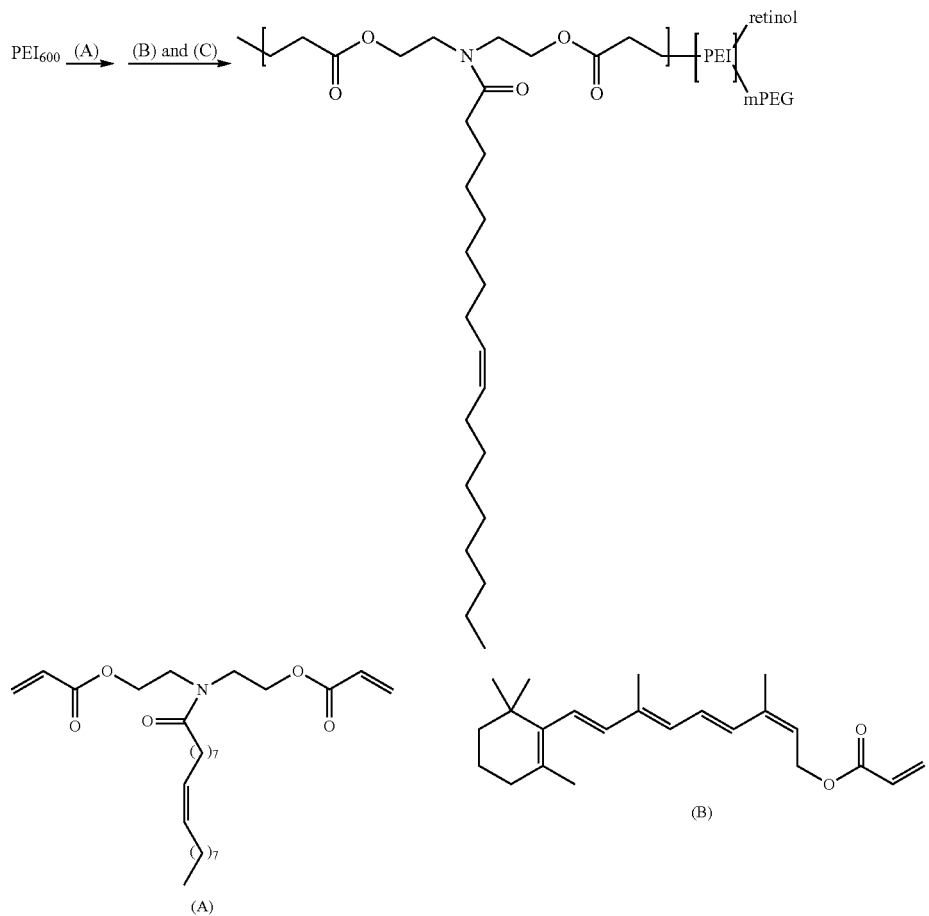

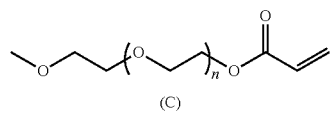

(C)

Synthesis of polymer 1 A solution of degradable lipid linker (A, 23.9 mg, mmol) in CH$_2$Cl$_2$/MeOH (1:2, 1.2 mL) was added to a solution of PEI$_{600}$ (15.0 mg, 0.025 mmol) in CH$_2$Cl$_2$/MeOH (1:2, 1 mL) while stirring. It was vigorously stirred at room temperature for 1 hour. Then a solution of acryloyl retinol (B, 3.4 mg, 0.01 mmol) in CH$_2$Cl$_2$/MeOH (1:2, 1 mL), and a solution of acryloyl polyethylene glycol (C, 18.2 mg, 0.04 mmol) in CH$_2$Cl$_2$/MeOH (1:2, 1 mL). After being vigorously stirred at room temperature for 2 more hours, it was cooled in ice water and quenched with 2M HCl/ether (0.5 mL) while stirring and cooled diethyl ether (−20° C.) to 45 mL. Precipitate formed. The solid product was obtained by centrifugation (5,000 rpm). Diethyl ether (30 mL) was added to the solid, and the suspension was centrifuged 1 more time. The final product was dried under reduced pressure at room temperature overnight to yield the desired product (60 mg, 80%). The product was confirmed by NMR spectroscopy.

Synthesis of polymer 2 A solution of degradable lipid linker (A, 47.8 mg, 0.075 mmol) in CH$_2$Cl$_2$/MeOH (1:2, 1.8 mL) was added to a solution of PEI$_{600}$ (15.0 mg, 0.025 mmol) in CH$_2$Cl$_2$/MeOH (1:2, 1 mL) while stirring. It was vigorously stirred at room temperature for 1 hour. Then a solution of acryloyl retinol (B, 3.4 mg, 0.01 mmol) in CH$_2$Cl$_2$/MeOH (1:2, 1 mL), and a solution of acryloyl polyethylene glycol (C, 18.2 mg, 0.04 mmol) in CH$_2$Cl$_2$/MeOH (1:2, 1 mL). After being vigorously stirred at room temperature for 2 more hours, it was cooled in ice water and quenched with 2M HCl/ether (0.5 mL) while stirring and cooled diethyl ether (−20° C.) to 45 mL. Precipitate formed. The solid product was obtained by centrifugation (5,000 rpm). Diethyl ether (30 mL) was added to the solid, and the suspension was centrifuged 1 more time. The final product was dried under reduced pressure at room temperature overnight to yield the desired product (60 mg, 80%). The product was confirmed by NMR spectroscopy.

Synthesis of polymer 3 A solution of degradable lipid linker (A, 47.8 mg, 0.10 mmol) in CH$_2$Cl$_2$/MeOH (1:2, 1.8 mL) was added to a solution of PEI$_{600}$ (15.0 mg, 0.025 mmol) in CH$_2$Cl$_2$/MeOH (1:2, 1 mL) while stirring. It was vigorously stirred at room temperature for 1 hour. Then a solution of acryloyl retinol (B, 3.4 mg, 0.01 mmol) in CH$_2$Cl$_2$/MeOH (1:2, 1 mL), and a solution of acryloyl polyethylene glycol (C, 18.2 mg, 0.04 mmol) in CH$_2$Cl$_2$/MeOH (1:2, 1 mL). After being vigorously stirred at room temperature for 2 more hours, it was cooled in ice water and quenched with 2M HCl/ether (0.5 mL) while stirring and cooled diethyl ether (−20° C.) to 45 mL. Precipitate formed. The solid product was obtained by centrifugation (5,000 rpm). Diethyl ether (30 mL) was added to the solid, and the suspension was centrifuged 1 more time. The final product was dried under reduced pressure at room temperature overnight to yield the desired product (60 mg, 80%). The product was confirmed by NMR spectroscopy.

Synthesis of polymer 4 A solution of degradable lipid linker (A, 47.8 mg, 0.125 mmol) in CH$_2$Cl$_2$/MeOH (1:2, 1.8 mL) was added to a solution of PEI$_{600}$ (15.0 mg, 0.025 mmol) in CH$_2$Cl$_2$/MeOH (1:2, 1 mL) while stirring. It was vigorously stirred at room temperature for 1 hour. Then a solution of acryloyl retinol (B, 3.4 mg, 0.01 mmol) in CH$_2$Cl$_2$/MeOH (1:2, 1 mL), and a solution of acryloyl polyethylene glycol (C, 18.2 mg, 0.04 mmol) in CH$_2$Cl$_2$/MeOH (1:2, 1 mL). After being vigorously stirred at room temperature for 2 more hours, it was cooled in ice water and quenched with 2M HCl/ether (0.5 mL) while stirring and cooled diethyl ether (−20° C.) to 45 mL. Precipitate formed. The solid product was obtained by centrifugation (5,000 rpm). Diethyl ether (30 mL) was added to the solid, and the suspension was centrifuged 1 more time. The final product was dried under reduced pressure at room temperature overnight to yield the desired product (60 mg, 80%). The product was confirmed by NMR spectroscopy.

Synthesis of polymer 5 A solution of a degradable monomeric reactant of Formula (VIIb) was prepared by dissolving 2.37 mg in a mixture of dichloromethane and methanol (1:2, 30 mL). A solution of branched PEI (MW=1200, 360 mg) in a mixture of dichloromethane and methanol (1:2, 3 mL) was added to the degradable monomeric reactant solution. The mixture solvent (5 mL) was added as a rinse into the reaction mixture. After addition was complete, the reaction mixture was stirred at room temperature for 2 hours. A solution of PEG (MW=454, 272.4 mg) in dichloromethane and methanol (1:2, 2 mL) was then added. The mixture solvent (3 mL) was added as a rinse into the reaction mixture. The reaction mixture was then stirred for another one hour. The reaction was then cooled in ice-water for 10 minutes before being quenched with a solution of 2 M hydrochloric acid in ether (270 mL) while stirring. The suspension was placed in eight 50-mL conical centrifuge tubes and diluted with additional cooled ether (−20° C.). The suspension in the tubes was centrifuged. The liquid was decanted, and the white solid product was washed with more ether and centrifuged twice. The product was dried under vacuum to yield 2.04 g (62%). The product, polymer 5 (degradable lipid unit:mPEI:PEG (12:1:2), was characterized by $^1$H-NMR.

Brief Summary of Polymers 1-5

| Polymer | PEI | Lipid Linker | Retinol | PEG |
|---|---|---|---|---|
| Polymer 1 | 0.025 mmol | 0.050 mmol | 0.01 mmol | 0.04 mmol |
| Polymer 2 | 0.025 mmol | 0.075 mmol | 0.01 mmol | 0.04 mmol |
| Polymer 3 | 0.025 mmol | 0.100 mmol | 0.01 mmol | 0.04 mmol |
| Polymer 4 | 0.025 mmol | 0.125 mmol | 0.01 mmol | 0.04 mmol |
| Polymer 5 | 0.300 mmol | 4.950 mmol | NA | 0.60 mmol |

Example 7 siRNA Transfection

Cells expressing Green Fluorescent Protein (GFP) were seeded to 96-well plates at a density of 1×10$^4$ cells per well one day before the transfection. A solution of siRNA (1.0 µg) was dissolved in distilled water and further diluted to 30 µl with OptiMEM (Invitrogen). The siRNA used in these experiments was anti-GFP (CGAGAAGCGCGAUCACAUGUU (SEQ ID NO: 3). The test polymer and control polymer was prepared at a concentration of 5 mg/mL, by dissolving the delivery reagents in appropriate amount of $dH_2O$. For Polymer 5, the polymer and retinol were mixed and prepared at a concentration of 5 mg/mL as described previously. The delivery reagent solutions were further diluted with OptiMEM to a final volume of 30 µL according to the compound to siRNA ratio. The diluted siRNA solution and the delivery reagent solutions were mixed and incubated at room temperature for 15 min. The mixture of the siRNA and the delivery reagents (15 µL) was added to each well of the pre-seeded cells, mixed, and incubated at 37° C. incubator with 5% $CO_2$. After 48 hours, transfection and efficiency cell viability were evaluated.

Example 8

Evaluation of Transfection Efficiency

The transfection was evaluated by measuring the expression of GFP under the fluorescence microscope. The absorbance of GFP was detected at 485-528 nm with the UV-vis microplate reader.

Example 9

Cell Uptake

Figure 4:
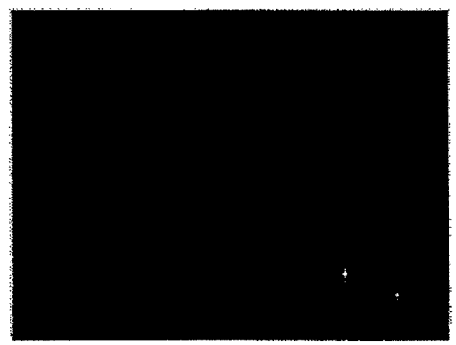
FIG. 4 illustrates cell uptake of siRNA into primary hepatic stellate cells.
Figure 4:
Figure 4:
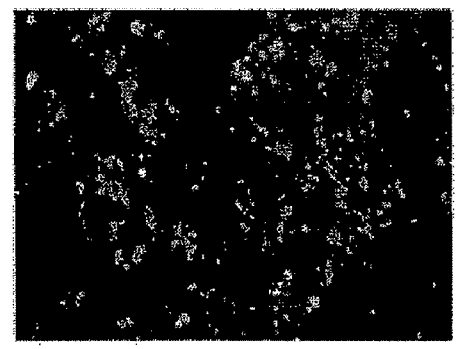

Primary hepatic stellate cells (HSC) NRK-49F cells were isolated from the liver tissues using the reported procedure (Houglum et al. "Two Different cis-acting Regulatory Regions Direct Cell-specific Transcription of the Collagen al (1) Gene in Hepatic Stellate Cells and in Skin and Tendon Fibroblasts." *J. Clin. Invest.* 1995, 96, 2269-2276). The isolated hepatic stellate cells were cultured in 6-well plate at seeding density of $3 \times 10^5/2$ mL/well with appropriate medium overnight. For Polymers 1-4, a solution of the test polymer was dissolved in Milli Q-$H_2O$ (5 mg/mL). For Polymer 5, a solution of the test polymer was dissolved in Milli Q-$H_2O$ (5 mg/mL) and mixed with a solution of all-trans retinol dissolved in dimethyl sulfoxide (DMSO, 28.65 mg/mL, approximately 100 mM) at 25:2.5, weight/weight ratio of retinol:test polymer. For all the polymers, the mixture was further diluted in 5% glucose to the final concentration of 0.17 mg/mL of test polymer. The mixture was vortexed for 20 seconds and allowed to stabilize at room temperature for 15 minutes. A solution of Cy3 labeled siRNA prepared in RNase-free water (0.25 mg/mL, approximately 20 mM) was added into the mixture (2.5:1 weight by weight ratio of test polymer 1:Cy3-siRNA. The mixture was further vortexed and incubated at room temperature for another 15 minutes. The mixture (100 µL) was added to primary HSC culture and continued incubation at 37° C. for another 4 hours. Then imaged was captured under fluorescence microscopy (Ex/Em: 532/554 nm). For the two controls, (a) a solution of retinol in DMSO (28.65 mg/mL) was added to a solution of solution of Cy3 labeled siRNA prepared in RNase-free water (0.25 mg/mL, approximately 20 mM) at the ratio of 25:1 weight by weight of retinol:Cy3-siRNA, and (b) a solution of test polymer dissolved in Milli Q-$H_2O$ (5 mg/mL) was added to a solution of Cy3 labeled siRNA prepared in RNase-free water (0.25 mg/mL, approximately 20 mM) at the ratio of 2.5:1 weight by weight of test polymer:Cy3-siRNA. The two mixtures were further diluted with 5% glucose and incubated at room temperature for 15 minutes. 100 mL of each mixture was added separately to primary HSC culture and incubated at 37° C. for four hours. The imaged was captured photographically under fluorescence microscopy (Ex/Em: 532/554 nm). The results are shown in FIG. 4. As shown by the photographs in FIG. 4, cells treated with the cationic polymer+siRNA+retinol took up more of the Cy3 chromophore as compared to cells treated with water soluble degradable crosslinked cationic polymer+siRNA or siRNA alone.

Example 10

Cell Viability Assay

Figure 5:
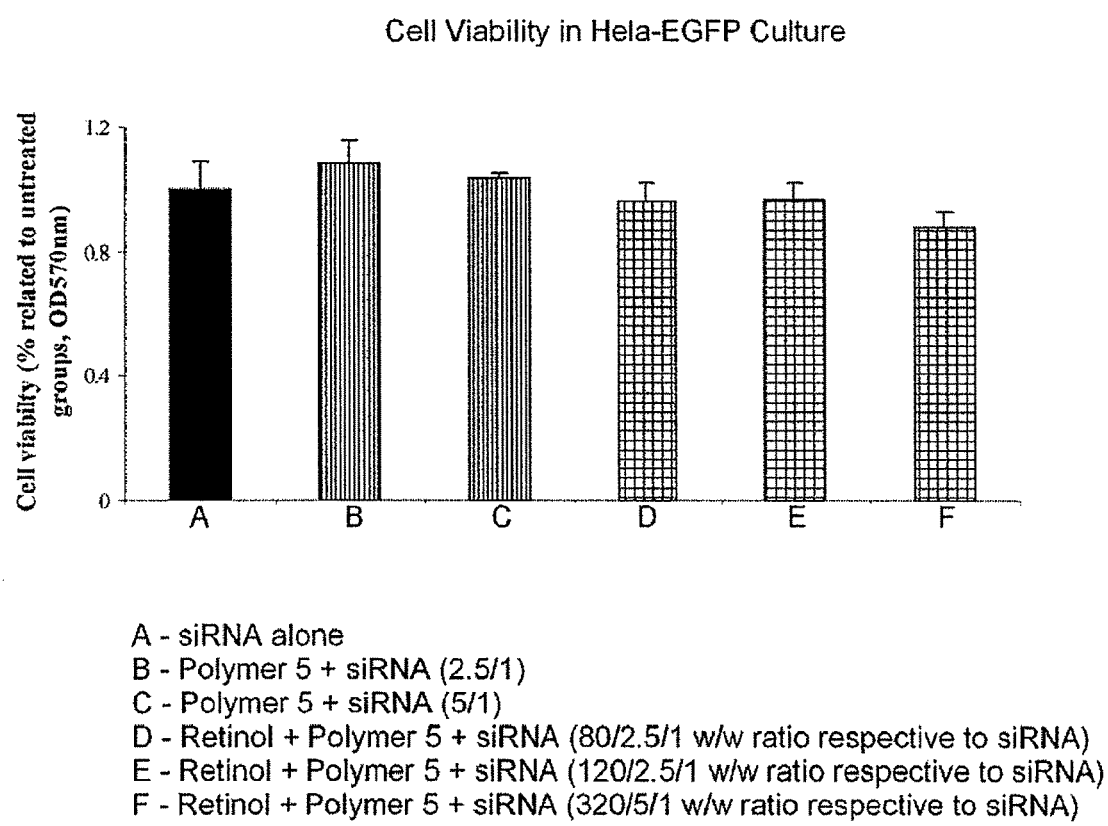
FIG. 5 is a bar graph showing cell viability of primary hepatic stellate cells (HSC) after being treated with siRNA alone, a water soluble degradable crosslinked cationic polymer+siRNA, or a water soluble degradable crosslinked cationic polymer+retinol+siRNA.

A solution of 3-(4,5-dimethylthiazol-2-yl)-2,5-diphenyltetrazolium bromide (MTT) was prepared by dissolving 250 mg of solid MTT in 50 mL of Dubecco PBS and stored at 4° C. After 48 hours of transfection, MTT solution (10 µL of the 5 mg/mL) was added to each well of the cells and incubated at 37° C. for 2-4 hours until purple crystal growth could be observed. Then solubilized solution (100 µL) was added and incubated at 37° C. overnight. The absorbance was detected at wavelength of 570 nm with the absorbance at 690 nm as reference. The results of cell viability assay are presented in FIG. 5. As shown in FIG. 5, cationic polymer+siRNA+retinol had comparable cytoxicity to cationic polymer+siRNA and siRNA alone.

Example 11

Figure 6:
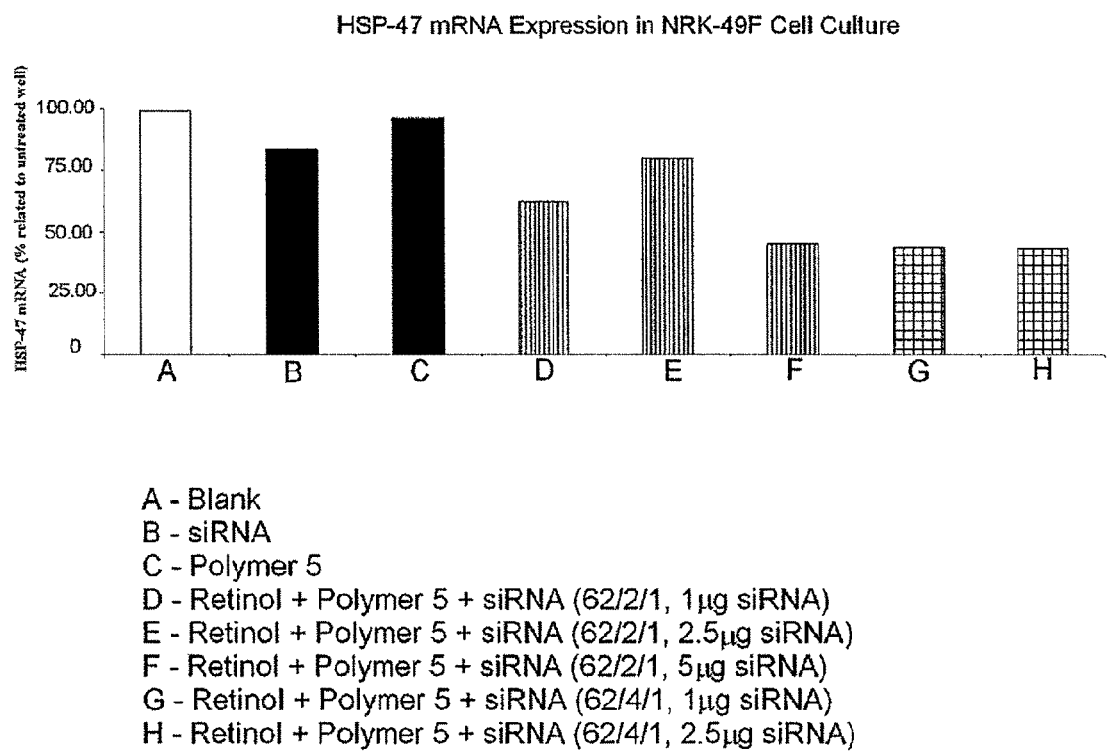
FIG. 6 is a bar graph showing the relative percentage of heat shock protein (HSP-47) mRNA after being treated with siRNA alone, a cationic polymer+siRNA or a cationic polymer+retinol+siRNA.
Figure 7:
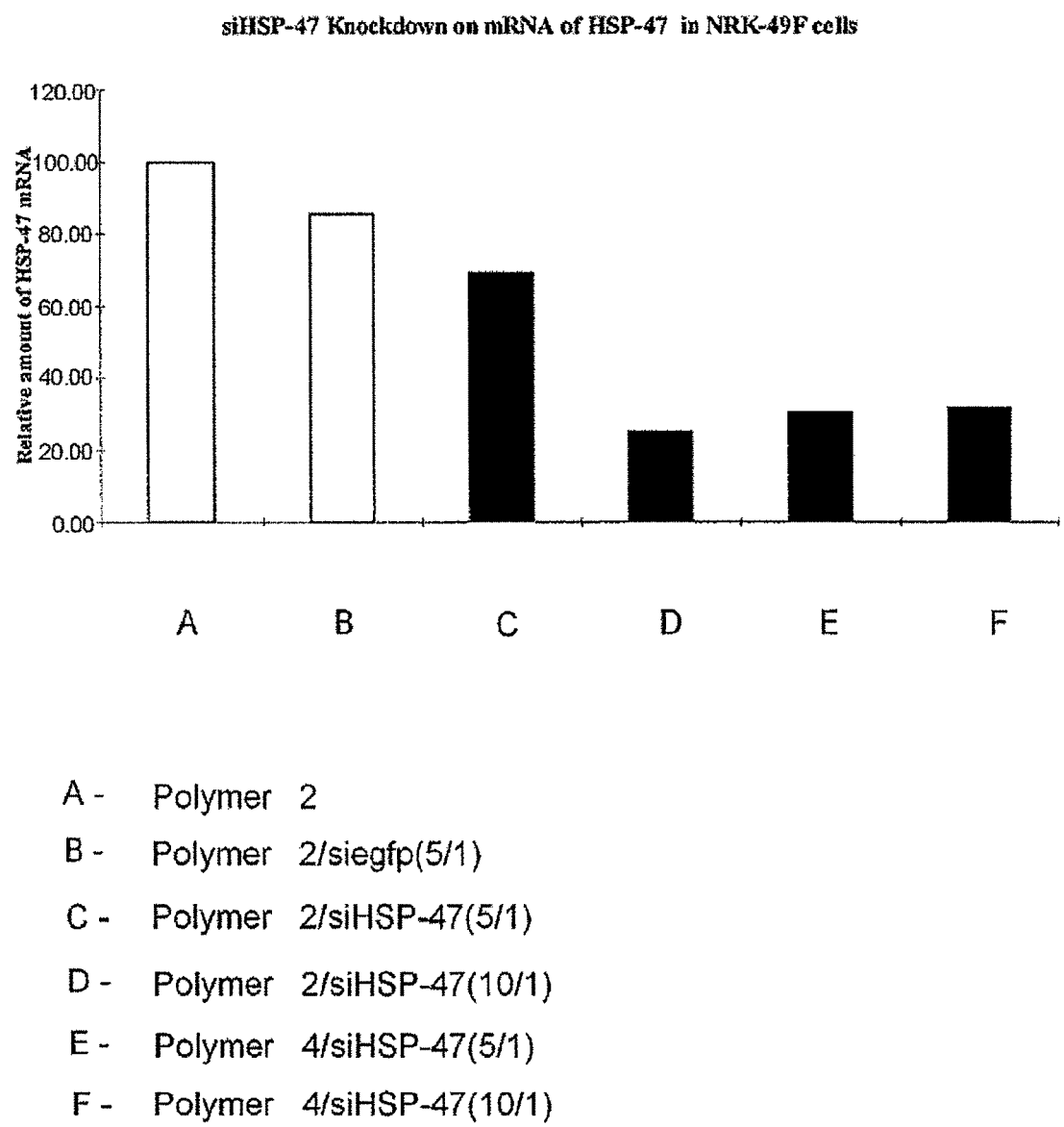
FIGS. 7 and 8 are bar graphs showing the relative percentage of heat shock protein (HSP-47) mRNA after being treated with a cationic polymer or a cationic polymer+siRNA.
Figure 8:
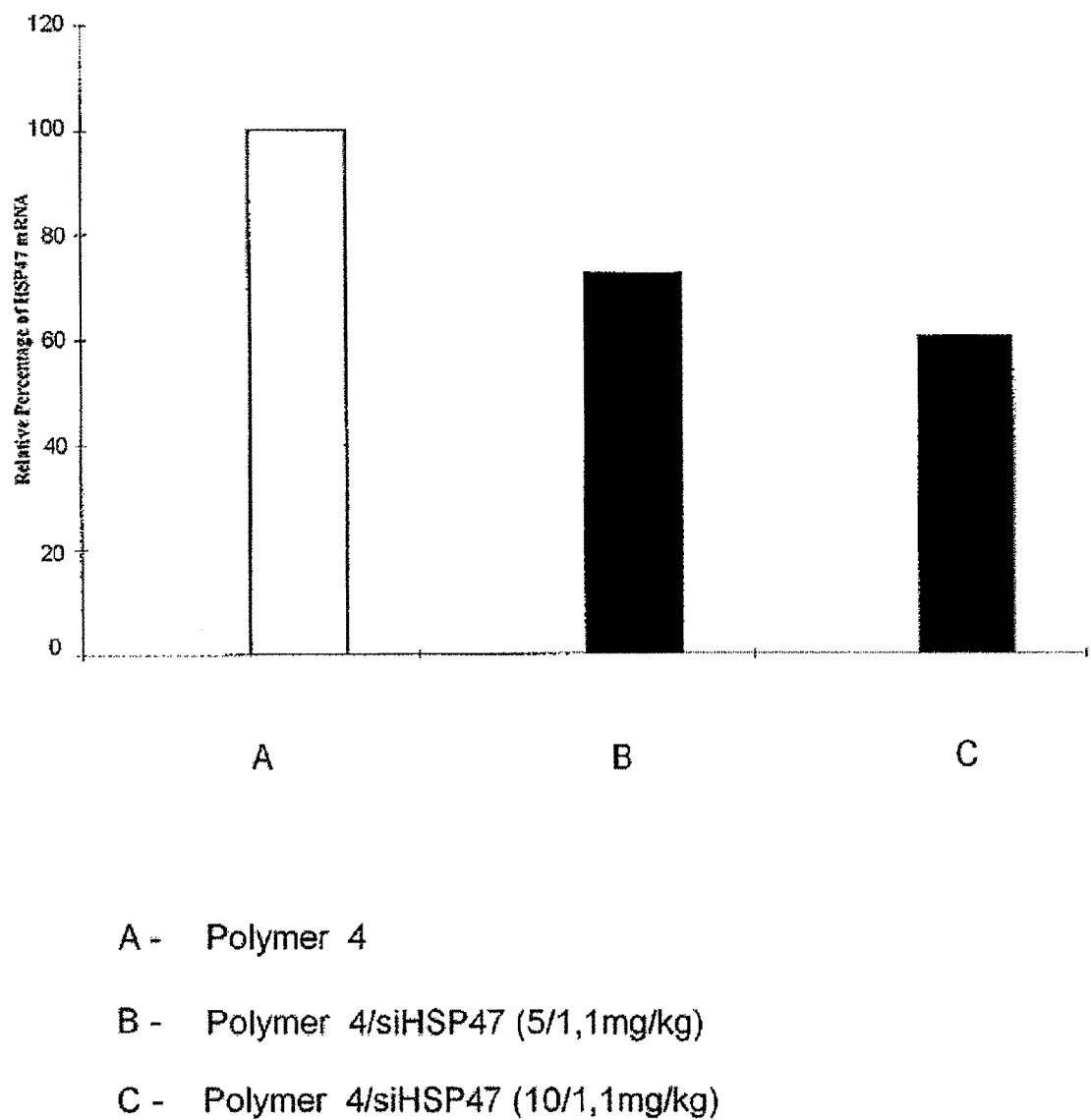

Normal rat kidney fibroblast cells (NRK-49f) was purchased from ATCC and cultured in 6-well plate at seeding density of $3 \times 10^5/2$ mL/well in DMEM medium containing 10% FBS, 1% penicillin and streptomycin overnight. siRNA targeting HSP-47 (heat shock protein) was purchased from Ambion, Inc. For Polymers 1-4, a solution of test polymer was dissolved in Milli Q-$H_2O$ (5 mg/mL). For Polymer 5, a solution of test polymer was dissolved in Milli Q-$H_2O$ (5 mg/mL) and mixed with a solution of all-trans retinol dissolved in dimethyl sulfoxide (DMSO, 28.65 mg/mL, approximately 100 mM) at various weight to weight ratios. For all of the polymers, the mixture was further diluted in 5% glucose to the final concentration of 0.17 mg/mL of test polymer. The mixture was further diluted in 5% glucose to the final concentration of 0.17 mg/mL of test polymer. The mixture was vortexed for 20 seconds and allowed to stabilize at room temperature for 15 minutes. A solution of siHSP-47 prepared in RNase-free water (0.25 mg/mL, approximately 20 mM) was added into the mixture at various weight to weight ratios. The mixture was further vortexed and incubated at room temperature for another 15 minutes. The mixture (200 µL) was added to primary HSC culture and continued incubation at 37° C. for another 48 hours. The cells were harvested 48 hours after transfection and the total RNA was extracted with RNeasy Mini Kit (Qiagen, Cat. No. #74104) and cDNA was synthesized with reversed transcript kit Superscript III First-Strand Synthesis System for RT-PCR (Invitrogen, Cat. No. #18080-051). Quantitative PCR for HSP-47 was conducted with Brilliant SYBR Green QPCR Mix (Stratagene, Cat. No. #600548) on Stratagene Mx3005P system with the primer: 5'-CAATGTGACCTGGAAACTGG-3' (forward) (SEQ ID NO: 4) and 5'-ATGAAGCCACGGTTGTCTAC-3', (SEQ ID NO: 5). The results are shown in FIGS. 6-8. As illustrated in FIGS. 6-8, the amount of mRNA produced decreases in cells treated with compositions that included cationic polymer+siRNA+retinol as compared to fibroblast cells treated with cationic polymer+siRNA or siRNA alone.

Example 12

LD50

Figure 9:
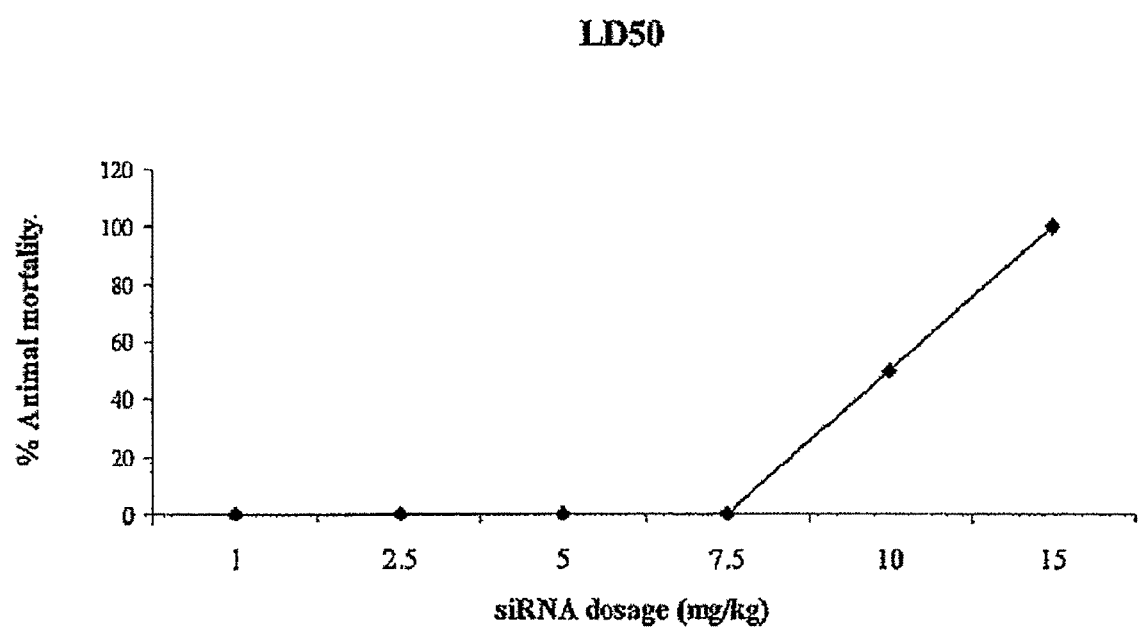
FIG. 9 illustrates the results of a LD50 determination.

Polymer 4 was dissolved in Milli Q-water at 50 µg/µl. siHSP47 was diluted with RNase-free water to 2000 µM (equivalent to approximately 25 μg/μl). Nu/nu male mice, 30 grams, was injected via tail vein single bolus injection with Polymer 4/siRNA complexes (weight to weight ratio of polymer 4/siRNA: 5/1, 200 μL) at various doses of siRNA: (1) 1 mg/kg, (2) 2.5 mg/kg, (3) 5 mg/kg, (4) 7.5 mg/kg, (5) 10 mg/kg, and (6) 15 mg/kg. The results are shown in FIG. 9. LD50 was found to be 10 mg/kg which is significantly higher than an exemplary therapeutic level of approximately 2-3 mg/kg.

Example 13

Hemolytic Assay

Figure 10:
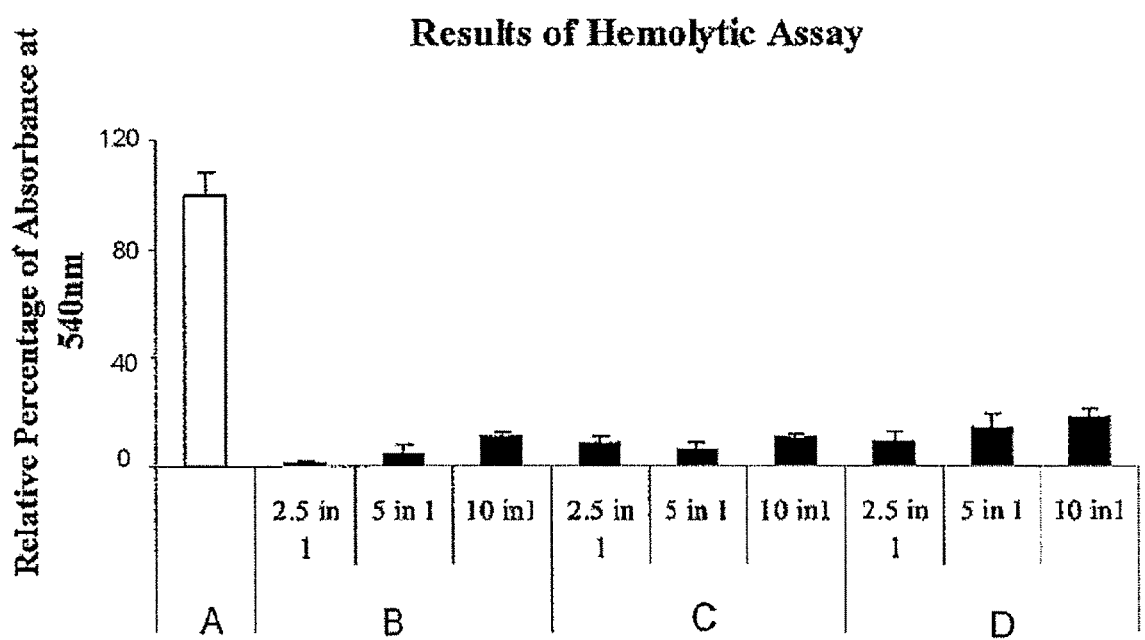
FIG. 10 illustrates the results of the hemolytic assay.

Blood samples of nude mice were collected in heparinize-tubes and were centrifuged at 700×g for 10 minutes. The supernatant was discarded, and the red blood cell pellet was washed three times with cold PBS (pH 7.4) and was re-suspended in the same buffer. Solutions of the polymers and the siEGFP of different concentrations were prepared in PBS buffers and were added to the round-bottom plate at 100 μL/well. Blood sample (10 μL) was added to each well, and the plate was incubated for 60 minutes at 37° C. The release of hemoglobin was determined by photospectrometric analysis after centrifugation (700 g for 10 min). The supernatant (100 μL) from each well was transferred into flat-bottom plate. Intensity of fluorescence at 540 nm was measured by a plate reader. The results are shown in FIG. 10. As shown in FIG. 10, complete hemolysis (i.e., red blood cell death) was achieved using 0.2% TritonX-100 (100 μL/well with 10 μL of blood sample), yielding the 100% control value, as indicated by the high absorbance at 540 nm. The polymers and siRNA complexes described herein demonstrated significantly lower absorbance, indicating that less than 10% hemolysis was achieved. This low degree of hemolysis suggests that the polymers and siRNA complexes described herein are relatively safe in animals.

It will be understood by those of skill in the art that numerous and various modifications can be made without departing from the spirit of the present invention. Therefore, it should be clearly understood that the forms of the present invention are illustrative only and not intended to limit the scope of the present invention.

What is claimed is:

1. A therapeutic compositions comprising:

A cationic polymeric carrier which comprises a recurring polyethylene glycol (PEG) unit; a recurring polyethyleneimine (PEI) unit; a targeting agent comprising a retinoid; and a recurring degradable unit, wherein the cationic polymeric carrier comprises the following structure:

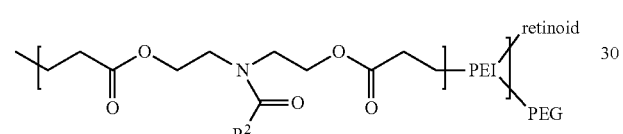

and a therapeutic agent operatively associated with the cationic polymeric carrier, wherein the therapeutic agent exhibits a therapeutic activity upon delivery to a target organ or tissue, and wherein the therapeutic activity is selected from the group consisting of inhibiting fibrosis within the target organ or tissue and inhibiting the growth of a cancer cell within the target organ or tissue;

wherein the $R^2$ is selected from the group consisting of oleyl, lauryl, myristyl, palmityl, margaryl, stearyl, arachidyl, behenyl, lignoceryl and a sterol.

2. The therapeutic composition of claim 1, wherein the cationic polymeric carrier comprises the following structure:

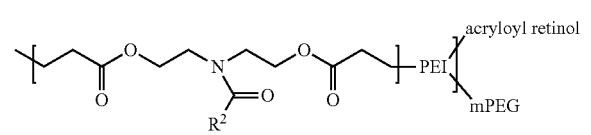

wherein the mPEG is methoxy polyethylene glycol.

3. The therapeutic composition of claim 1, wherein $R^2$ is oleyl.

4. The therapeutic composition of claim 1, wherein the cationic polymeric carrier comprises the following structure:

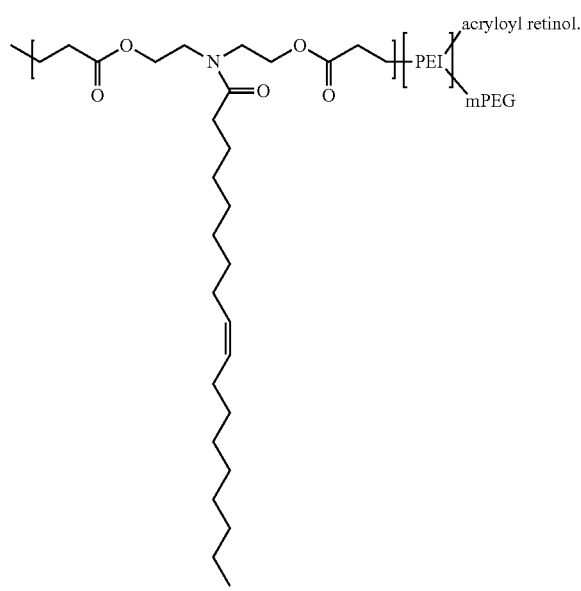

5. The therapeutic composition of claim 1, wherein the target organ is selected from the group consisting of liver, pancreas, kidney, lung, esophagus, larynx, bone marrow, and brain.

6. The therapeutic composition of claim 1, wherein the targeting agent provides an increase in the delivery selectivity of the therapeutic composition, upon delivery to the target organ or tissue, that is at least about two-fold as compared to that of an otherwise comparable therapeutic composition without the targeting agent.

7. The therapeutic composition of claim 6, wherein the increase in delivery selectivity is at least about 3-fold.

8. The therapeutic composition of claim 1, wherein the recurring polyethyleneimine (PEI) unit has a structure selected from the group consisting of Formula (II), (III), (IV), (V) and (VI),

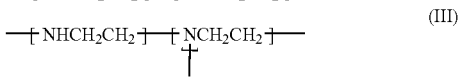

-continued

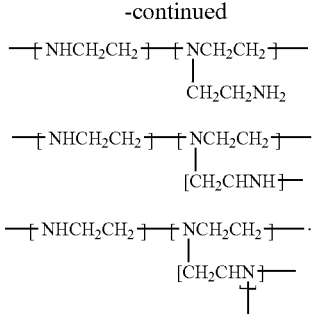

9. The therapeutic composition of claim 1, wherein the recurring polyethyleneimine (PEI) unit is selected from the group consisting of a linear polyethyleneimine recurring unit and a branched polyethyleneimine recurring unit.

10. The therapeutic composition of claim 1, wherein $R^2$ is selected from the group consisting of oleyl, lauryl, myristyl, palmityl, margaryl, stearyl, arachidyl, behenyl, and lignoceryl.

11. The therapeutic composition of claim 1, wherein $R^2$ is a sterol.

12. The therapeutic composition of claim 1, wherein the recurring degradable unit has the following structure:

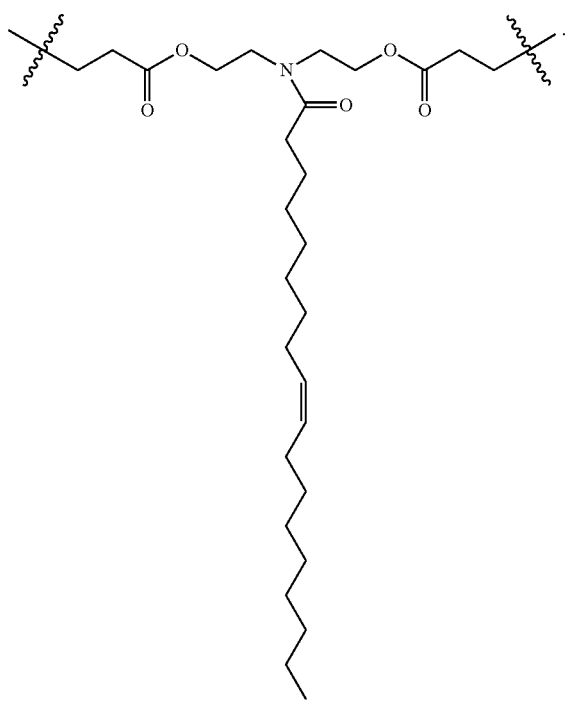

13. The therapeutic composition of claim 1, wherein the cationic polymeric carrier is a microparticle.

14. The therapeutic composition of claim 1, wherein the cationic polymeric carrier is a nanoparticle.

15. The therapeutic composition of claim 1, wherein the therapeutic agent, upon delivery to the target organ or tissue, inhibits the activity of an agent selected from the group consisting of a tissue inhibitor of metalloproteinases (TIMP) and a molecular chaperone, wherein the molecular chaperone is HSP47.

16. The therapeutic composition of claim 1, wherein the therapeutic agent is selected from the group consisting of siRNA, DNA, RNA, and an antisense nucleic acid.

17. The therapeutic composition of claim 1, wherein the therapeutic agent is an anti-cancer agent.

18. The therapeutic composition of claim 1, further comprising at least one selected from a pharmaceutically acceptable excipient and a diluent.

19. A method for treating a condition characterized at least in part by abnormal fibrosis, comprising administering a therapeutically effective amount of the therapeutic composition of claim 1 to a subject in need thereof.

20. The method of claim 19, wherein the condition is selected from the group consisting of cancer and a fibrotic disease.

21. The method of claim 19, wherein the condition is hepatic fibrosis.

22. The method of claim 19, wherein the condition is pancreatic cancer.

23. The therapeutic composition of claim 1, wherein the therapeutic agent is siRNA.

24. The therapeutic composition of claim 1, wherein the recurring polyethylene glycol (PEG) unit has a molecular weight of about 464 Daltons.

25. The therapeutic composition of claim 1, wherein the recurring polyethyleneimine (PEI) unit is a branched polyethyleneimine (PEI) recurring unit.

26. The therapeutic composition of claim 1, wherein the recurring polyethyleneimine (PEI) unit has a molecular weight of about 1200 Daltons.

* * * * *

UNITED STATES PATENT AND TRADEMARK OFFICE
CERTIFICATE OF CORRECTION

PATENT NO. : 8,003,621 B2
APPLICATION NO. : 12/210098
DATED : August 23, 2011
INVENTOR(S) : Yoshiro Niitsu et al.

It is certified that error appears in the above-identified patent and that said Letters Patent is hereby corrected as shown below:

Title Page:

At (Item 56) Column 2, Line 47, Under Other Publications, please change "Mannosa" to --Mannose--.

At (Item 56) Page 3, Column 2, Line 4, Under Other Publications, please change "877·887," to --877-887,--.

At (Item 56), Page 3, Column 2, Line 34, Under Other Publications, please change "phosphateyinsulin-like" to --phosphateinsulin-like--.

At (Item 56), Page 3, Column 2, Lines 43-44, Under Other Publications, please change "succinamide):" to --succinimide):--.

At (Item 56), Page 3, Column 2, Line 73, Under Other Publications, please change "254·257," to --254-257,--.

In the Specifications:

At Column 2, Line 62, Please change "1000 mm" to --1000 nm--.

At Column 2, Line 66, Please change "1 nm n in" to --1 nm in--.

At Column 4, Line 4, Please change "cycloalkyl cycloalkenyl" to --cycloalkyl, cycloalkenyl--.

At Column 6, Line 48, Please change "heteroalicyclic" to --heterocyclyl--.

At Column 6, Line 60, Please change "4-piperidonyl," to --4-piperidinyl,--.

At Column 7, Line 8 (Approx.), Please change "substitutent" to --substituent--.

At Column 10, Line 1, please change "$(CH_2)_{p1}\text{-}E\text{-}(CH_2)_{p2}\text{--}$" to -- $-(CH_2)_{p1}\text{-}E\text{-}(CH_2)_{p2}-$ --.

At Column 10, Line 8, please change "$C_4\text{-}C_{24}$ alkenyl, $C_4\text{-}C_{24}$ alkynyl" to --$C_8\text{-}C_{24}$ alkenyl, $C_8\text{-}C_{24}$ alkynyl--.

Signed and Sealed this
Twenty-eighth Day of May, 2013

Teresa Stanek Rea
*Acting Director of the United States Patent and Trademark Office*

CERTIFICATE OF CORRECTION (continued)
U.S. Pat. No. 8,003,621 B2

At Column 16, Line 38, please change "[N-2-aminoethyl]ethylene" to --[N-(2-aminoethyl)ethylene--.

At Column 16, Line 39, please change "(N-cholesteryloxycabonyl" to --(N-cholesteryloxycarbonyl--.

At Column 23, Line 5, please change "PEI with" to --with PEI--.

At Column 23, Line 6, please change "one or moieties" to --one or more moieties--.

At Column 25, Line 48, please change "soya" to --soya oil--.

At Column 37, Line 12, please change "and efficiency" to --efficiency and--.

At Column 37, Line 28, please delete "NRK-49F cells.".

At Column 37, Line 53, please change "Then imaged" to --The image--.

At Column 37, Lines 55-56, please change "a solution of solution of" to --a solution of--.

At Column 37, Line 64, please change "100 mL" to --100 µL--.

At Column 37, Line 66, please change "imaged" to --image--.

At Column 38, Line 21, please change "cytoxicity" to --cytotoxicity--.

At Column 38, Line 45 (Approx.), please change "primary HSC culture" to --NRK-49F cells culture--.

In the Claims:

At Column 41, Line 18, In Claim 1, please change "compositions" to --composition--.

At Column 41, Line 19, In Claim 1, please change "A" to --a--.

At Column 41, Line 45 (Approx.), In Claim 1, after "wherein" delete "the".

SEQUENCE LISTING

```
<160> NUMBER OF SEQ ID NOS: 5

<210> SEQ ID NO 1
<211> LENGTH: 21
<212> TYPE: RNA
<213> ORGANISM: Artificial Sequence
<220> FEATURE:
<223> OTHER INFORMATION: siRNA sequence derived from serine protease
      inhibitor

<400> SEQUENCE: 1
gcaacuaaag accuggaugu u                                              21

<210> SEQ ID NO 2
<211> LENGTH: 21
<212> TYPE: RNA
<213> ORGANISM: Artificial Sequence
<220> FEATURE:
<223> OTHER INFORMATION: siRNA sequence derived from serine protease
      inhibitor

<400> SEQUENCE: 2
cucguugauu ucuggaccua c                                              21

<210> SEQ ID NO 3
<211> LENGTH: 21
<212> TYPE: RNA
<213> ORGANISM: Artificial Sequence
<220> FEATURE:
<223> OTHER INFORMATION: siRNA synthetic sequence derived from Aequorea
      victoria

<400> SEQUENCE: 3
cgagaagcgc gaucacaugu u                                              21

<210> SEQ ID NO 4
<211> LENGTH: 20
<212> TYPE: RNA
<213> ORGANISM: Artificial Sequence
<220> FEATURE:
<223> OTHER INFORMATION: HSP-47 Primer

<400> SEQUENCE: 4
```

```
caaugugacc uggaaacugg                                               20

<210> SEQ ID NO 5
<211> LENGTH: 20
<212> TYPE: RNA
<213> ORGANISM: Artificial Sequence
<220> FEATURE:
<223> OTHER INFORMATION: HSP-47 Primer

<400> SEQUENCE: 5
augaagccac gguugucuac                                               20
```